United States Patent
Yoshino

(10) Patent No.: US 11,219,362 B2
(45) Date of Patent: Jan. 11, 2022

(54) FUNDUS IMAGING APPARATUS

(71) Applicant: NIDEK CO., LTD., Aichi (JP)

(72) Inventor: Masayuki Yoshino, Aichi (JP)

(73) Assignee: NIDEK CO., LTD., Aichi (JP)

( * ) Notice: Subject to any disclaimer, the term of this patent is extended or adjusted under 35 U.S.C. 154(b) by 182 days.

(21) Appl. No.: 16/457,038

(22) Filed: Jun. 28, 2019

(65) Prior Publication Data

US 2020/0000335 A1 Jan. 2, 2020

(30) Foreign Application Priority Data

| Jul. 2, 2018 | (JP) | JP2018-126408 |
| Jul. 2, 2018 | (JP) | JP2018-126409 |
| Mar. 29, 2019 | (JP) | JP2019-067253 |
| Mar. 29, 2019 | (JP) | JP2019-067254 |

(51) Int. Cl.
*A61B 3/12* (2006.01)
*A61B 3/15* (2006.01)

(52) U.S. Cl.
CPC ............. *A61B 3/12* (2013.01); *A61B 3/152* (2013.01)

(58) Field of Classification Search
CPC ......... A61B 3/12; A61B 3/152; A61B 3/0025; G06T 2207/20221; G06T 2207/20224; G06T 2207/30041; G06T 5/50
USPC ........................................................ 351/206
See application file for complete search history.

(56) References Cited

U.S. PATENT DOCUMENTS

| 10,149,615 | B2 * | 12/2018 | Sakai | A61B 3/0091 |
| 2011/0051089 | A1 * | 3/2011 | Wada | A61B 3/12 351/208 |
| 2014/0333896 | A1 * | 11/2014 | Ueno | A61B 3/10 351/211 |
| 2017/0049323 | A1 * | 2/2017 | Bublitz | A61B 3/14 |

FOREIGN PATENT DOCUMENTS

| EP | 3 235 421 A1 | 10/2017 | |
| EP | 3235421 A1 * | 10/2017 | ........... A61B 3/1025 |
| EP | 3 257 433 A1 | 12/2017 | |
| JP | 61-048940 B2 | 10/1986 | |
| JP | 2014-233325 A | 12/2014 | |

OTHER PUBLICATIONS

Search Report dated Nov. 15, 2019 by the European Patent Office in counterpart European Patent Application No. 19183761.6.

\* cited by examiner

*Primary Examiner* — Mohammed A Hasan
(74) *Attorney, Agent, or Firm* — Sughrue Mion, PLLC

(57) ABSTRACT

A fundus imaging apparatus acquires a fundus image based on a signal from a light receiving element that receives fundus reflection light of illumination light with which a fundus of a subject eye is irradiated through an objective lens. The fundus imaging apparatus includes an information acquisition unit that acquires information relating to a refractive power of a subject eye, and a process that executes an artifact suppressing process for suppressing occurrence of an artifact due to reflection of the illumination light at the objective lens. The processor switches an imaging mode based on the refractive power between an invalid mode in which the artifact suppressing process is not executed and a valid mode in which the artifact suppressing process is executed.

9 Claims, 15 Drawing Sheets

FUNDUS IMAGING APPARATUS

CROSS-REFERENCE TO RELATED APPLICATION

This application claims priority from Japanese Patent Applications No. 2018-126408 filed on Jul. 2, 2018, No. 2018-126409 filed on Jul. 2, 2018, No. 2019-067253 filed on Mar. 29, 2019 and No. 2019-067254 filed on Mar. 29, 2019, the entire subject-matter of which is incorporated herein by reference.

TECHNICAL FIELD

The present disclosure relates to a fundus imaging apparatus for obtaining a front image of a fundus.

BACKGROUND

A fundus imaging apparatus for capturing a front image of a fundus of a subject eye has been widely used in an ophthalmic field. As the fundus imaging apparatus, the following apparatuses may be used, including a fundus camera or a scan type laser ophthalmoscope. For example, JP-B-S61-48940 discloses an apparatus that scans slit-shaped illumination light on the fundus and sequentially projects an image of an illuminated fundus region onto a two-dimensional imaging plane in accordance with the scan, to obtain a fundus front image. In most of the fundus imaging apparatuses, light projection and reception of the illumination light is performed through an objective lens.

In the fundus imaging apparatus having such an objective lens, there is a possibility that reflected light generated in a front or rear surface of the objective lens may be back-ground-reflected as an artifact in a fundus image, under at least a part of imaging conditions. Such an artifact appears as a bright spot image (reflected image) in the vicinity of the center of the fundus image. A bright spot image may lead to failure in diagnosis and observation.

SUMMARY

An object of the present disclosure is to provide a fundus imaging apparatus capable of acquiring a fundus image in which an artifact is suppressed.

The fundus imaging apparatus of the present disclosure includes the following configurations.

There is provided a fundus imaging apparatus that has an imaging optical system including an irradiation optical system configured to irradiate a fundus of a subject eye with illumination light through an objective lens and a light receiving optical system configured to share the objective lens with the irradiation optical system and include a light receiving element that receives fundus reflection light of the illumination light, and acquires a fundus image based on a signal from the light receiving element, including:

a refractive power information acquisition unit configured to acquire refractive power information that is information relating to a refractive power of a subject eye; and a processor configured to execute an artifact suppressing process of suppressing occurrence of an artifact due to reflection of the illumination light on the objective lens, in which the processor switches an imaging mode between an invalid mode in which the artifact suppressing process is not executed in capturing a fundus image and a valid mode in which the artifact suppressing process is executed in capturing a fundus image, based on the refractive power.

DETAILED DESCRIPTION

<Overview>

Figure 1:
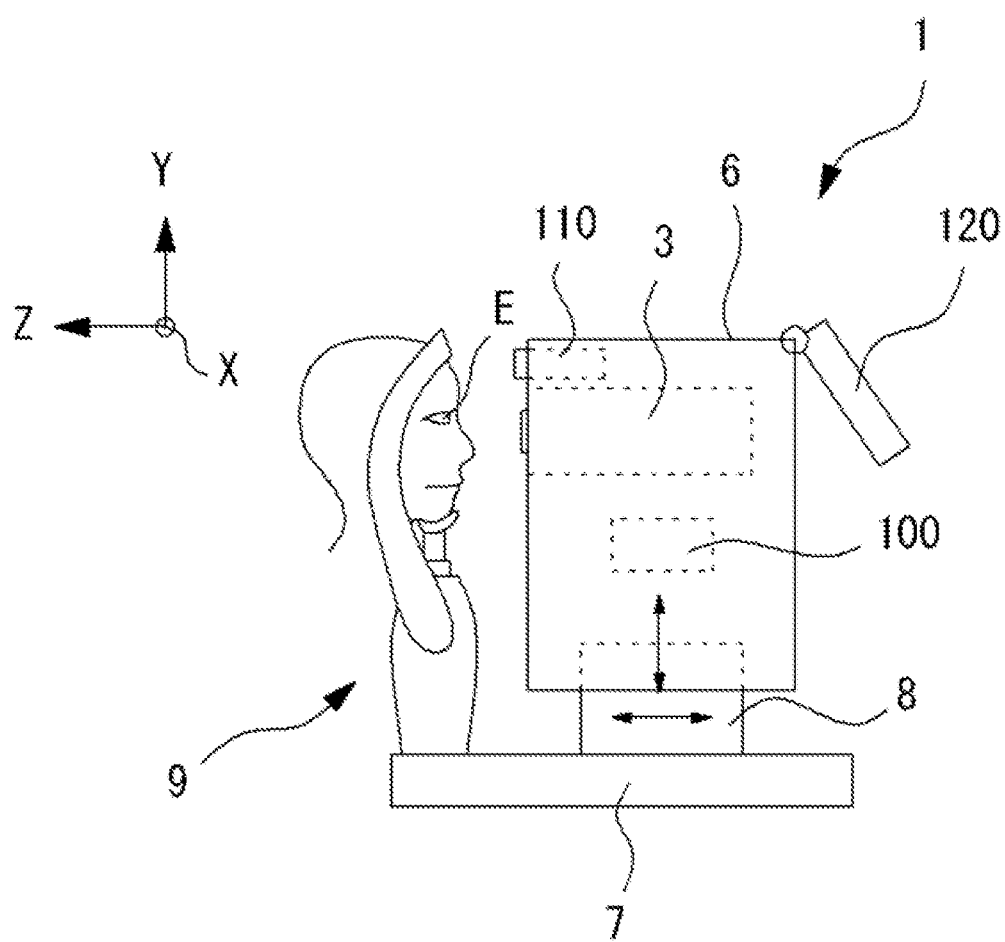
FIG. 1 is a diagram showing an external configuration of an apparatus according to an example.

Hereinafter, embodiments of a fundus imaging apparatus according to the present disclosure will be described with reference to the drawings. Hereinafter, in each of first to third embodiments, an apparatus in which an artifact generated by reflection and scattering inside a subject eye or the apparatus is suppressed is disclosed. Each embodiment may appropriately use a part or all of the other embodiments.

First Embodiment

First, a first embodiment will be described. In the first embodiment, a fundus imaging apparatus (see FIG. 1) includes at least an imaging optical system (e.g., see FIG. 2), and a control unit (e.g., see FIG. 3). The fundus imaging apparatus may additionally include a refractive power information acquisition unit.
<Control Unit>

The control unit is a processing unit (processor) that performs a control processing of each unit and an arithmetic processing in the fundus imaging apparatus. For example, the control unit is realized by a CPU (Central Processing Unit), a memory, and the like. In this embodiment, the control unit may also serve as an image processing unit (imaging processor). The image processing unit may execute at least one of generation of a fundus image or a variety of image processing for the fundus image.
<Imaging Optical System>

The imaging optical system is used for projection and reception of illumination light with respect to the fundus of a subject eye through an objective lens to capture a fundus image. In the first embodiment, the imaging optical system includes an irradiation optical system, a light receiving optical system, and a diopter correction optical system (see FIGS. 2, 4A, and 4B).

The irradiation optical system irradiates the fundus of the subject eye with illumination light through the objective lens. Additionally, the irradiation optical system may have a light source (illumination light source) that emits illumination light. The light receiving optical system has a light receiving element for receiving fundus reflection light of illumination light. The light receiving optical system forms an image of the fundus based on the fundus reflection light of the illumination light on an imaging plane. A signal from the light receiving element is input to the image processing unit. In the image processing unit, the image formed on the imaging plane is acquired (generated) based on the signal from the light receiving element, as a fundus image. In the present disclosure, a front image of the fundus is referred to as a "fundus image".

The irradiation optical system and the light receiving optical system share at least the objective lens. Further, the irradiation optical system and the light receiving optical system may share an optical path coupler. The optical path coupler couples and decouples a light projection optical path of illumination light and a light receiving optical path of fundus reflection light. In this case, the objective lens is disposed on a common optical path of the light projection optical path and the light receiving optical path formed by the light path coupler.

The imaging optical system may be a scan type optical system that performs imaging by scanning illumination light on the fundus. The imaging optical system may be a non-scan type optical system. As an example of the scan type optical system, a spot scanning type optical system and a line scan type optical system may be used. In the spot scan type optical system, spot-shaped illumination light is two-dimensionally scanned on the fundus. In the line scan type optical system, line-shaped illumination light is scanned in one direction. The line-shaped illumination light may be linearly scanned on the fundus, or may be rotationally scanned on the fundus, for example. In the case of the rotary scan, the center of rotation may be an optical axis of the imaging optical system (hereinafter, may be referred to as an "imaging optical axis"). In the scan type optical system, any one of a point light receiving element, a line sensor, a two-dimensional light receiving element (imaging element), and the like may be appropriately employed as the light receiving element. Further, as an example of the non-scan type optical system, an optical system of a general fundus camera, or the like may be used.
<Diopter Correction Optical System>

The diopter correction optical system (FIGS. 2, 4A, and 4B) is used for correcting a diopter of the imaging optical system in accordance with a refractive power of the subject eye. The refractive power of the subject eye is also referred to as a refractive error and a diopter value. In this embodiment, the diopter correction optical system adjusts independently a diopter correction amount in the irradiation optical system (hereinafter, referred to as an "irradiation-side correction amount") and a diopter correction amount in the light receiving optical system (hereinafter, referred to as a "light receiving-side correction amount").

The diopter correction optical system may be disposed separately in two or more positions of the imaging optical system. In this case, the diopter correction optical system may have a first diopter correction optical system and a second diopter correction optical system. A diopter correction amount in the first diopter correction optical system and a diopter correction amount in the second diopter correction optical system are independently set. For example, the first diopter correction optical system may be disposed on an optical path of one of the irradiation optical system and the light receiving optical system, and in this case, the second diopter correction optical system may be disposed on an optical path of the other one thereof with respect to the one optical path, or may be disposed on a common optical path of the irradiation optical system and the light receiving optical system.

In this embodiment, a first drive unit (first driver) and a second drive unit (second driver) may be provided. The first drive unit and the second drive unit are independently controlled by the control unit. The first drive unit drives at least one optical element included in the first diopter correction optical system. Further, the second drive unit drives at least one optical element included in the second diopter correction optical system.

In a case where the second diopter correction optical system is disposed on the common optical path, the diopter correction amount in the other optical system is defined by a sum of the diopter correction amount in the first diopter correction optical system and the diopter correction amount in the second diopter correction optical system. For convenience of description, one or both that affect the diopter of the irradiation optical system, among the first diopter correction optical system and the second diopter correction optical system, may be referred to as a "irradiation-side diopter correction optical system", one or both that affect the diopter of the light receiving optical system may be referred to as a "light receiving-side diopter correction optical system."

Figure 4A:
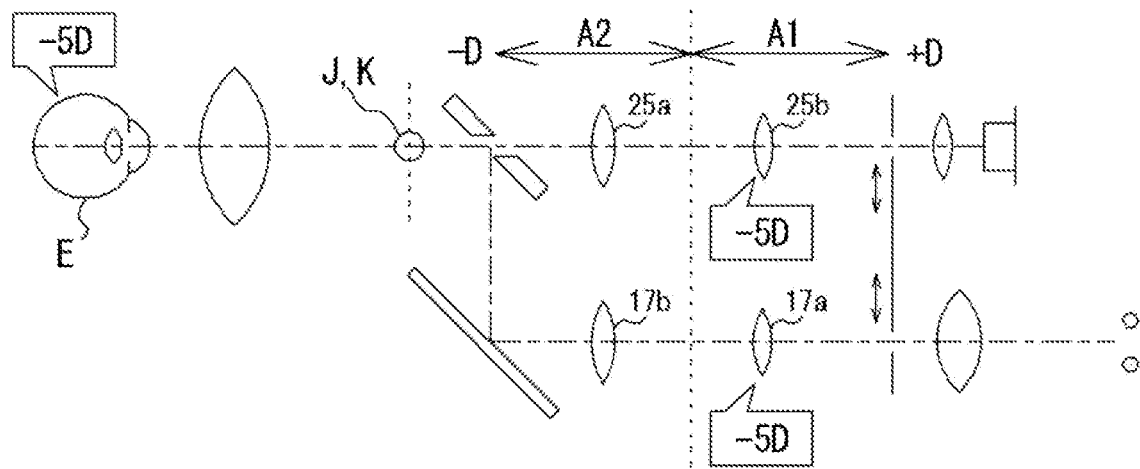
FIG. 4A is a diagram for explaining an operation of a diopter correction optical system in accordance with a refractive power of a subject eye, which shows a state of diopter correction in a case where the refractive power is in a first range.
Figure 4B:
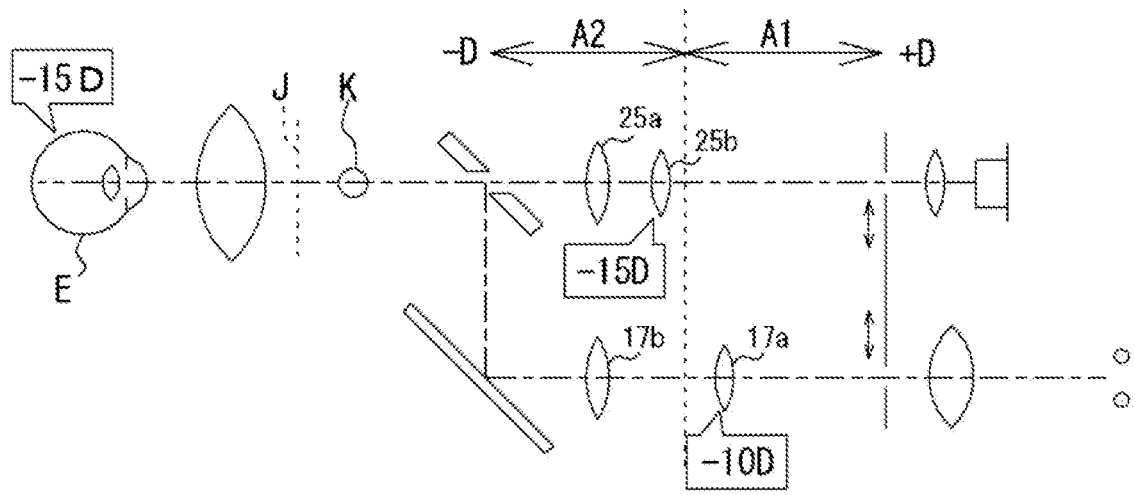
FIG. 4B is a diagram for explaining the operation of the diopter correction optical system in accordance with the refractive power of the subject eye, which shows a state of diopter correction in a case where the refractive power is in a second range.

However, a position that conjugates with the fundus with respect to the objective lens (that is, a position of an intermediate image plane of the fundus) is displaced in accordance with the refractive power (mainly, a spherical degree) of the subject eye. In FIGS. 4A and 4B, the position of the intermediate image plane is indicated by a reference sign J. In this embodiment, as the diopter correction optical system disposed between the objective lens and the imaging plane is driven so that the intermediate image plane and the imaging plane of the light receiving optical system are in a conjugate relationship, the fundus image is preferably formed on the imaging plane.

In the present disclosure, the "conjugate" should not be necessarily limited to a complete conjugate relationship, and may include "approximately conjugate". That is, a case in which the position is displaced from the complete conjugate position in a range permitted in relation to a technical significance of each unit is also included in the "conjugate" in the present disclosure.

Further, in a case where the diopter correction is also performed in the irradiation optical system, for example, it may be considered that an error of an illumination range is suppressed or a light amount distribution of illumination light on the fundus is easily uniformized. However, a condensing position in the irradiation optical system is displaced along the optical axis, depending on the irradiation-side correction amount. Specifically, as the irradiation-side correction amount is shifted to a negative diopter side, the condensing position is considered to approach the objective lens. In FIGS. 4A and 4B, the condensing position is indicated by a reference sign K. As the condensing position approaches the surface of the objective lens (i.e., a front surface or a rear surface), reflection of the illumination light from the objective lens may be easily glared on the fundus image as an artifact. That is, in a case where the irradiation-side correction amount is adjusted in accordance with the refractive power, as the refractive power of the subject eye is closer to a value closer to the negative diopter side (for example, in the case of myopia with higher strength), the artifact easily occurs.

<Artifact Suppression Due to Mismatch of Irradiation-Side Correction Amount and Light Receiving-Side Correction Amount>

In this regard, the control unit may control the diopter correction optical system to adjust the irradiation-side correction amount and the light receiving-side correction amount to different values (see FIG. 4B). For example, the control unit may adjust the light receiving-side correction amount in accordance with the refractive power of the subject eye. More specifically, the light receiving-side correction amount may be adjusted to a diopter that is approximately the same as the refractive power.

In this case, the control unit may adjust the condensing position of the illumination light through the diopter correction optical system with reference to the intermediate image of the fundus which is formed through the objective lens (see FIG. 4B). More specifically, the irradiation-side correction amount may be adjusted so that the condensing position is away farther from the objective lens with respect to the intermediate image. Thus, the fundus image is easily satisfactorily imaged with respect to the imaging plane, and generation of artifacts due to reflection on the objective lens is suppressed. As a result, a good fundus image is captured.

Here, the irradiation-side correction amount may be adjusted to have an absolute value smaller than that of the light receiving-side correction amount. As a difference between the irradiation-side correction amount and the light receiving-side correction amount becomes larger, various effects such as reduction of the light receiving optical amount easily occur. Therefore, by limiting each correction amount so that a large difference between the irradiation-side correction amount and the light receiving-side correction amount does not occur, it is possible to obtain a fundus image of high quality while suppressing the occurrence of artifacts.

In a case where the irradiation-side correction amount and the light receiving-side correction amount are adjusted to different values, the control unit may adjust the irradiation-side correction amount to a constant value regardless of the light receiving-side correction amount. Here, the invention is not limited to such a configuration, in the same case, the irradiation-side correction amount may be adjusted to a different value for each light receiving-side correction amount.

Here, it is not essential that the adjustment is always performed in each imaging so that the irradiation-side correction amount and the light receiving-side correction amount are set to different values. For example, in predetermined imaging conditions, the irradiation-side correction amount and the light receiving-side correction amount may match each other. Here, the imaging conditions where an artifact does not make a problem may be examined in advance by experiments, optical simulations, or the like. For example, a diopter correction amount range in which an artifact does not occur in a state where the irradiation-side correction amount and the light receiving-side correction amount match each other may be determined in advance as an imaging condition. In a case where the irradiation-side correction amount and the light receiving-side correction amount match each other, each of the irradiation-side correction amount and the light receiving-side correction amount may be adjusted to a diopter that is approximately same as the refractive power.

<Switching of Imaging Mode in Accordance with Refractive Power>

The control unit in this embodiment may perform switching of an imaging mode of the apparatus between a first imaging mode and a second imaging mode in accordance with the refractive power of the subject eye. In the second imaging mode, the diopter correction optical system is controlled so that a "difference value" is increased, compared with the first imaging mode. The difference value refers to the difference between the irradiation-side correction amount and the light receiving-side correction amount. As an example, in the first imaging mode, imaging may be performed in a state where the irradiation-side correction amount and the light receiving-side correction amount match each other (see FIG. 4A). In this case, both of the irradiation-side correction amount and the light receiving-side correction amount may be adjusted to values depending on the refractive power. Further, in the second imaging mode, imaging may be performed in a state where the irradiation-side correction amount and the light receiving-side correction amount are made different from each other (see FIG. 4B). In this case, as an example, the control unit may adjust the light receiving-side correction amount in accordance with the refractive power of the subject eye, and may set the irradiation-side correction amount to a value of which an absolute value is smaller than that of the light receiving-side correction amount.

The refractive power of the subject eye may be broadly divided into a first range and a second range on a negative diopter side with respect to the first range. The second range is a range where an intermediate image plane of fundus reflection light formed through the objective lens (mainly, an intermediate image plane formed closest to the objective lens) is closer to the rear surface of the objective lens with respect to the first range. In FIGS. 4A and 4B, a range of the diopter correction amount corresponding to the first range is a range indicated by a reference sign A1. Further, a range of the diopter correction amount corresponding to the second range is a range indicated by a reference sign A2.

Between a case where the refractive power is in the first range and a case where the refractive power is in the second range, the imaging mode may be switched. The control unit may switch the imaging mode to the first imaging mode in a case where the refractive power is in the first range. Further, the control unit may switch the imaging mode to the second imaging mode in a case where the refractive power is in the second range.

A value of the refractive power that is a threshold of the first range and the second range may be examined in advance by experiments, optical simulations, or the like, for example. For example, in a case where the diopter correction amount in the diopter correction optical system changes from a positive diopter side to a negative diopter side while making the irradiation-side correction amount and the light receiving-side correction amount match each other, a value in which an artifact due to reflection from the objective lens starts to occur may be defined as the threshold.

<Scan Type Imaging Optical System>

Herein, as the scan type imaging optical system, an apparatus that includes a harmful light removing unit and a scanning unit (scanner) is known. In the scan type imaging optical system, the irradiation optical system forms a local illumination region in a part of the imaging range on the fundus. As a typical example, an apparatus that forms an illumination region in a slit shape or a spot shape is known.

The harmful light removing unit is disposed on the optical path of the light receiving optical system with the diopter correction optical system being interposed between the objective lens and the harmful light removing unit. In this case, the harmful light removal unit may be disposed at a position that conjugates with the fundus with respect to at least the objective lens and the diopter correction optical system, in a state where the light receiving-side correction amount corresponding to the refractive power of the subject eye is set.

The harmful light removing unit receives fundus reflection light from a local imaging region that is a part of the imaging range (hereinafter, referred to as a "valid region") by the light-receiving element. Further, the harmful light removing unit is used to remove light from a region other than the valid region. The harmful light removing unit may be an aperture, for example. As a typical aperture in the spot scan type apparatus, a pinhole may be used, and as a typical aperture in the slit scan type apparatus, a slit may be used. In this case, fundus reflection light from the valid region corresponding to an opening of the aperture of the entire imaging range in the fundus is selectively guided to the light-receiving element, and is acquired as a valid image. In particular, in the slit scan type apparatus, there is a case where the light-receiving element is used as the harmful light removing unit. In this case, as the light-receiving element, a line sensor may be used, or a complementary metal-oxide semiconductor (CMOS) with a rolling shutter function may be used. The shape itself of the line sensor is a slit shape. Further, in the CMOS with the rolling shutter function, line exposure is performed on a two-dimensional imaging plane. In the entire imaging range of the fundus, as fundus reflection light from a valid region corresponding to valid pixels of a line shape is selectively guided to the imaging plane, an image of the valid region is captured.

The scanning unit scans the local illumination region and the valid region (local imaging region) on the fundus in synchronization. For example, the scanning unit may be an optical scanner that is shared between the irradiation optical system and the light receiving optical system. In this case, the optical scanner is disposed on the common optical path between the irradiation optical system and the light receiving optical system.

Further, the scanning unit may include a first scanning unit provided in the irradiation optical system, and a second scanning unit that is a separate body from the first scanning unit and is provided in the light receiving optical system. In this case, in one example of the slit scan type apparatus, in order to form the local illumination region in a slit shape, a first slit-shaped member (an example of an aperture) may be disposed on the optical path of the irradiation optical system. The first scanning unit may include the first slit-shaped member, and a drive unit that moves the first slit-shaped member in a direction that intersects an optical axis. Furthermore, in a case where a second slit-shaped member is used as the harmful light removing unit, the second scanning unit may include the second slit-shaped member (an example of an aperture) and a drive unit that moves the second slit-shaped member in the direction that intersects the optical axis. The drive unit of the first scanning unit and the drive unit of the second scanning unit may be separate devices, or may be a common device.

Further, in the slit scan type apparatus, in a case where the CMOS is used as the light-receiving element, the second scanning unit may also be used by the CMOS. That is, the line exposure by the rolling shutter function may be controlled in synchronization with the first scanning unit. In this case, the CMOS that is the light-receiving element also serves as the harmful light removing unit and the second scanning unit. With this configuration, the number of parts of the optical system is reduced.

<Suppression of Image Height Change Associated with Diopter Correction>

In the above-described scan type imaging optical system, in a case where a positional deviation occurs between the illumination region and the valid region on the fundus, there is a possibility that the amount of received light is reduced or an image cannot be obtained at all.

In this regard, the diopter correction optical system may include a telecentric optical system. The telecentric optical system maintains an image height in a region on an image side with reference to the diopter correction optical system, in each of the irradiation optical system and the light receiving optical system, between a case where the irradiation-side correction amount and the light receiving-side correction amount match each other and a case where the irradiation-side correction amount and the light receiving-side correction amount are different from each other. However, here, in both of the irradiation optical system and the light receiving optical system, a subject eye side is referred to as an object side, and a side opposite to the subject eye with the diopter correction optical system being interposed therebetween is referred to as the image side. Even in a case where the irradiation-side correction amount and the light receiving-side correction amount do not match each other, the positional deviation between the illumination region and the valid region on the fundus does not easily occur by the telecentric optical system. Accordingly, the telecentric optical system has an effect capable of satisfactorily capturing a fundus image in a case where the occurrence of artifacts is suppressed, in the apparatus having the scan type imaging optical system. However, telecentricity of the optical system of this embodiment may be incomplete in an allowable accuracy range.

More specifically, the telecentric optical system may include a first telecentric optical system and a second telecentric optical system. The first telecentric optical system maintains an image height in the region on the image side with reference to the diopter correction optical system, regardless of a change in the light receiving-side correction amount. The second telecentric optical system maintains a ray height of main rays of the illumination light on the fundus, regardless of a change in the irradiation-side correction amount.

Further, in a non-scan type imaging optical system, similarly, the telecentric optical system is useful. That is, a magnification change of the fundus image associated with the diopter correction and a change of illumination unevenness are suppressed by the telecentric optical system.

<Adjustment of Imaging Conditions in Accordance with Diopter Correction Amount>

As a result of adjustment of the irradiation-side correction amount to a value different from the light receiving-side correction amount, for example, the following phenomena may occur. For example, there may be a case where an outer edge of a region where illumination light is emitted on the fundus is blurred. Further, there may be a case where a position of the region where the illumination light is emitted deviates from the position of the valid region. In a case where these phenomena occur, compared with the case where the irradiation-side correction amount and the light receiving-side correction amount match each other, the amount of received light easily decreases.

On the other hand, in this embodiment, between the first imaging mode and the second imaging mode, the control unit may change at least one of the amount of illumination light emitted toward the fundus, a gain of the light-receiving element, or an exposure time. More specifically, with respect to the first imaging mode, in the second imaging mode, at least one of the amount of the illumination light, the gain of the light-receiving element, or the exposure time is increased. Thus, even in a state where the irradiation-side correction amount and the light receiving-side correction amount do not match each other, it is possible to obtain a fundus image of a wide dynamic range. In order to increase the exposure time, the control unit may delay a scan speed. Further, in an apparatus that captures one image by consecutively capturing a plurality of fundus images and adding up a plurality of images, it is possible to substantially increase the exposure time by increasing the number of fundus images used for the addition.

<Refractive Power Acquisition Unit>

A refractive power information acquisition unit acquires refractive power information, as information relating to the refractive power of the subject eye.

For example, the refractive power information acquisition unit may be a measurement unit. In this case, as a result of measurement with respect to the subject eye, the refractive power information is acquired.

In the measurement unit that is the refractive power information acquisition unit, at least a part of the imaging optical system may be used. For example, the refractive power information acquisition unit may detect a focusing state in the light receiving optical system, and may acquire refractive power information on the basis of a detection result of the focusing state. More specifically, the focusing state may be detected while changing the light receiving-side correction amount that is the diopter correction amount in the light receiving optical system, and a value of the light receiving-side correction amount in the case of the most preferable focusing state may be acquired as the refractive power information. However, the refractive power information is not necessarily limited to the light receiving-side correction amount. For example, any one of the driving amount in the drive unit operated to change the light receiving-side correction amount (or the irradiation-side correction amount) and position information of the optical element which is displaced by the drive unit, or the like may be used as the refractive power information.

The focusing state may be detected on the basis of the fundus image acquired through the imaging optical system. In this case, the focusing state may be detected as contrast information of the fundus image. Further, the focusing state may be detected on the basis of the fundus image in which an index image of a focus index is background-reflected. As an example of the focus index, a split index is known (see FIG. 2). The split index is projected to the fundus as two index images that are separated by a prism. The focusing state may be detected on the basis of a positional relationship between the two index images. In this case, the refractive power information acquisition unit includes an index projecting unit that projects the focus index.

The refractive power information acquisition unit is not necessarily limited to the measurement unit. For example, the refractive power information acquisition unit may be configured to receive refractive power information that is measured in advance by a separate apparatus from the fundus imaging apparatus as an input, to obtain the refractive power information. In this case, the refractive power information acquisition unit may include the control unit, a port, and the like. The port is used for connecting any one of a separate apparatus, an external storage medium, a user interface, and the like to an ophthalmic measurement apparatus. As the separate apparatus, for example, a subjective type refraction test apparatus or an objective type refraction test apparatus may be used. The external storage medium may store refractive power information in advance. The control unit may read out the refractive power information from the storage medium to obtain the refractive power information. Further, the user interface may be used to manually input the refractive power information. In this case, the refractive power information may be acquired as an input result from an examiner.

<Adjustment of Difference Value Between Irradiation-Side Correction Amount and Light Receiving-Side Correction Amount in Consideration of Pupil Diameter>

A positional relationship between the pupil of the subject eye, and a light projection region and a light reception region in the imaging optical system may be changed in accordance with the size of the pupil of the subject eye. In this disclosure, a region where illumination light is projected on the pupil of the subject eye is referred to as the "light projection region", and similarly, a region where fundus reflection light from the illumination light on the pupil is extracted is referred to as the "light reception region".

As an example, a clearance between the light projection region and the light reception region may be changeable. By narrowing the clearance, it is possible to easily image a small pupil eye. However, in this case, in a case where the clearance is narrowed, an artifact based on the reflected light from the objective lens easily occurs.

As another example, an alignment position relating to XY directions (vertical and horizontal directions) may be changeable. In a case where vignetting occurs in a part of the light projection region and the light reception region, in a small pupil eye, an alignment reference position in the XY directions may be appropriately changed. As an alignment state is appropriately changed, the balance of light projection and light reception may be improved. However, a range of the diopter correction amount, in which the artifact based on the reflected light from the objective lens occur, may be changed depending on the alignment state in the XY directions.

In this regard, the control unit may adjust the difference value between the irradiation-side correction amount and the light receiving-side correction amount in accordance with the size of the pupil of the subject eye. For example, in the case of a first pupil diameter, the difference value may be adjusted to a first difference value, and in the case of a second pupil diameter smaller than the first pupil diameter, the difference value may be adjusted to a second difference that is larger than the first difference value (see FIG. 5). Thus, even in a case where the positional relationship between the pupil of the subject eye, and the light projection region and the light reception region in the imaging optical system is changed in accordance with the size of the pupil of the subject eye, it is possible to capture a fundus image in which an artifact is suppressed. The control unit may control the difference value in conjunction with the control of the above-described positional relationship.

In a case where the difference value is adjusted in accordance with the size of the pupil, the fundus imaging apparatus may further include a pupil information acquisition unit that acquires information indicating the size of the pupil (referred to as pupil information). The pupil information acquisition unit may include, for example, an anterior eye segment imaging optical system that captures an anterior eye segment image of the subject eye, and an image processing unit that acquires pupil information from the anterior eye segment image.

Second Embodiment

Next, a second embodiment will be described.

A fundus imaging apparatus according to the second embodiment executes a process for suppressing artifacts due to reflection at an objective lens (hereinafter, referred to as an artifact suppressing process). In the second embodiment, the artifact suppressing process is automatically executed in a case where the refractive power of the subject eye is included in a predetermined range. On the other hand, in a case where the refractive power is out of the range, the artifact suppressing process is not executed. In this way, in the second embodiment, the control unit performs switching of an imaging mode on the basis of the refractive power between an invalid mode in which the artifact suppressing process is invalid in capturing a fundus image (that is, the process is not executed) and a valid mode in which the artifact suppressing process is valid in capturing a fundus image (that is, the process is executed).

As described in the first embodiment, in a case where the diopter correction depending on the refractive power is performed in both the irradiation optical system and the light receiving optical system, as the refractive power is closer to a negative diopter side, an artifact more easily occurs. In the second embodiment, among a case where the refractive power is included in a first range and a case where the refractive power is included in a second range (on a negative diopter side with reference to the first range), in the former case, the imaging mode may be set to the invalid mode, and in the latter case, the imaging mode may be set to the valid mode. As a result, regardless of the refractive power of the subject eye, it is possible to obtain a fundus image in which occurrence of an artifact is suppressed. Further, in imaging a subject eye in which the refractive power is relatively on a positive diopter side, and thus, an artifact does not easily occur, it is possible to prevent at least one of the influence on the fundus image based on the artifact suppressing process, the burden of a subject in imaging, or the like.

A driving process of the diopter correction optical system for setting the irradiation-side correction amount (diopter correction amount in the irradiation optical system) and the light receiving-side correction amount (diopter correction amount in the light receiving optical system) to the different state in the first embodiment may be used as one example of various artifact suppressing processes. However, the artifact suppressing process in the second embodiment is not necessarily limited thereto. For example, in the artifact suppressing process, a plurality of fundus images in which positions of artifacts with respect to tissues of a subject eye are different from each other may be captured, and the plurality of fundus images may be combined to generate a composite image (for example, the following second to sixth artifact suppressing processes). Further, various operations shown in the following description may be employed.

Hereinafter, a detailed configuration of the second embodiment will be described with reference to different parts from the first embodiment. The fundus imaging apparatus according to the second embodiment includes at least an imaging optical system, an image processing unit, a refractive power acquisition unit, and a control unit. With respect to each of these configurations, items of <Control unit>, <Image processing unit>, <Imaging optical system>, and <Refractive power acquisition unit> in the above description of the first embodiment may be appropriately employed.

<Second Artifact Suppressing Process>

In the second artifact suppressing process, a fundus image is captured at least twice by changing a positional relationship between an imaging optical axis and a visual axis of a subject eye. Further, a plurality of fundus images obtained by at least two imaging operations are combined by the image processing unit. As a result, the apparatus obtains a composite image that is a fundus image in which an artifact is suppressed (see FIG. 6). In FIGS. 6 to 11, an artifact is indicated by a reference sign N, or by a reference sign N1 or N2. The image processing unit complements a region including an artifact in at least one (referred to as a first fundus image) of the plurality of fundus images using an image region of a different fundus image, which has the same positional relationship as that of the former region with respect to a fundus tissue, to thereby generate a composite image. More specifically, the region including the artifact in at least one of the plurality of fundus images may be replaced by a corresponding image region in the different image. Further, the region including the artifact may be complemented by image addition of the plurality of fundus images.

In order to perform the second artifact suppressing process, the fundus imaging apparatus may include a position adjusting unit. The position adjusting unit changes the positional relationship between the imaging optical axis and the visual axis of the subject eye, to thereby adjust an occurrence position of an artifact with respect to a fundus tissue in a fundus image. The position adjusting unit may include a fixation optical system. The fixation optical system presents a fixation target onto the subject eye. The fixation optical system may change a presentation position of the fixation target to a plurality of positions in a direction that intersects the imaging optical axis. Further, the position adjusting unit may include a drive unit that moves the imaging optical system with respect to the subject eye. For example, the drive unit rotates the imaging optical system around the anterior eye segment of the subject eye to change the positional relationship between the imaging optical axis and the visual axis of the subject eye. The position adjusting unit may include both of the fixation optical system and the drive unit.

For more details about the second artifact suppressing process, for example, see JP-A-2017-184787 filed by the present applicant.

<Third Artifact Suppressing Process>

Figure 7:
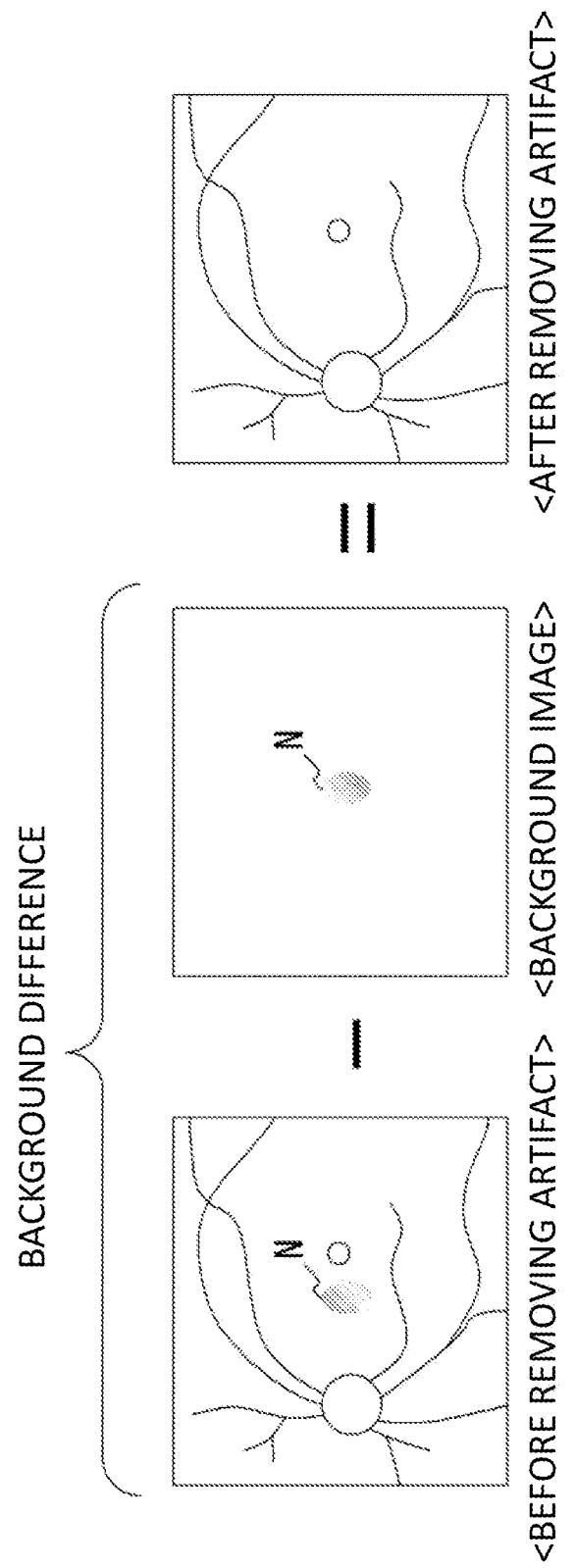
FIG. 7 is a diagram for explaining an outline of a third artifact suppressing process.

In the third artifact suppressing process, a background difference based on a fundus image and a background image is performed by the image processing unit, and as a result, the fundus image in which an artifact is suppressed is generated (see FIG. 7). The background image is a background image with respect to the fundus image, and includes at least an artifact due to the objective lens. The background image may be an image captured in a state where the front side of the objective lens is covered with a lid such as a lens cover.

For more details about the third artifact suppressing process, for example, see JP-A-2017-217076 filed by the present applicant.

<Apparatus Configuration that Becomes Premise of Fourth and Fifth Artifact Suppressing Processes>

Both of the fourth and fifth artifact suppressing processes are premised on the following configuration of an imaging optical system. That is, the imaging optical system may be a slit scan type optical system. For example, the imaging optical system may be the optical system shown in FIG. 2. The imaging optical system includes at least a slit forming unit, a scanning unit, and a light projection and reception separating unit. Additionally, the imaging optical system may include a light source, an imaging element, an optical path branching unit, and the like.

The slit forming unit forms illumination light in a slit shape on the fundus of a subject eye. The slit forming unit may be configured so that a slit-shaped light transmitting portion (for example, an opening) is disposed in a plane that conjugates with the fundus, for example.

Figure 2:
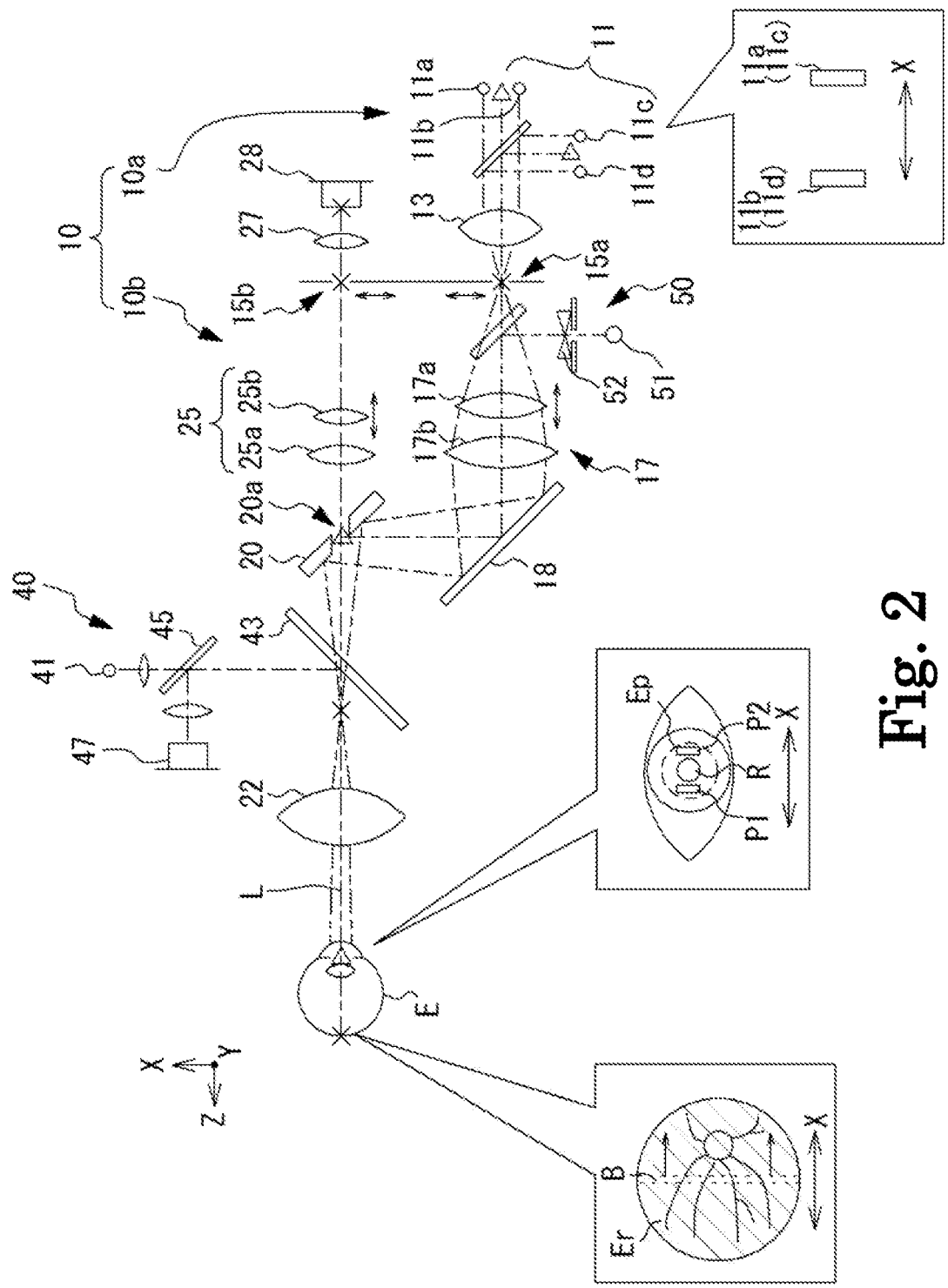
FIG. 2 is a diagram showing an optical system contained in an imaging unit, according to a first example.
Figure 8:
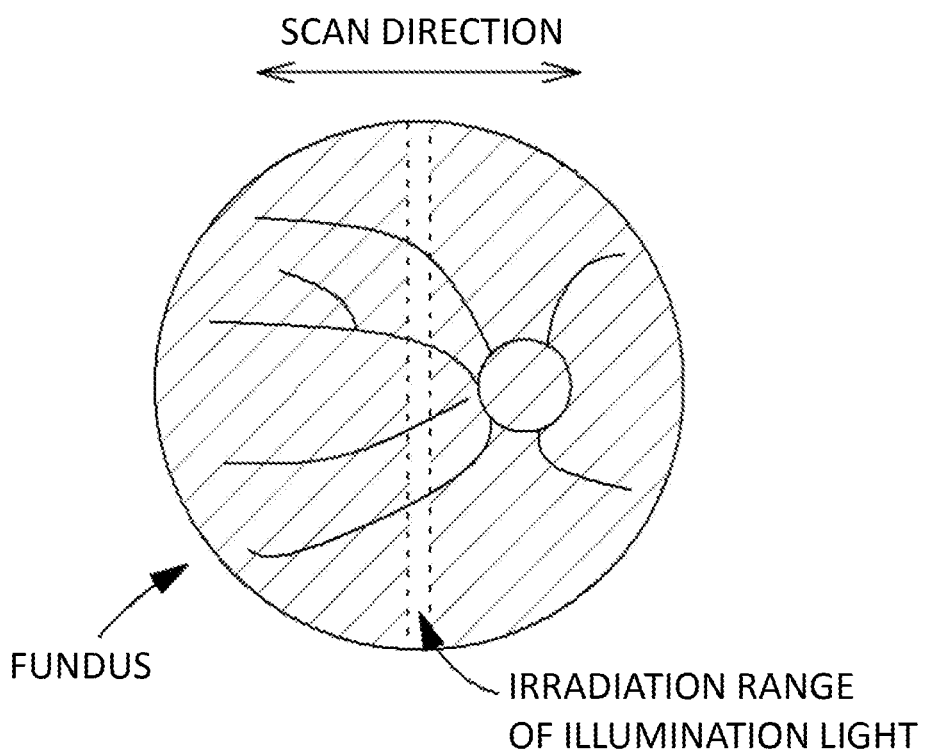
FIG. 8 is a diagram showing an aspect of irradiation and scan of illumination light on the fundus in the optical system shown in FIG. 2.

As shown in FIGS. 2 and 8, the scanning unit scans the illumination light formed in the slit shape on the fundus in a direction that intersects a slit (specifically, a direction that intersects a longitudinal direction of the slit). The scanning unit may move the slit forming unit in the direction that intersects the slit to scan the illumination light. As such a scanning unit, a mechanical shutter, a liquid crystal shutter, an optical chopper (see FIG. 12), a drum reel, or the like may be employed.

A scanning direction of the slit is preferably a direction that is perpendicular to the slit. However, the scanning direction may be a direction that is oblique to the perpendicular direction to the slit.

Further, the scanning unit may be a member that changes a direction of light that passes through the slit forming unit. For example, various optical scanners such as a galvanometer scanner may be used as the scanning unit. The scanning unit of a type that turns light to perform scan, as exemplified as a galvanometer scanner, may be disposed at a position that conjugates with the pupil of the subject eye.

The imaging optical system may further include an optical path coupler and an objective lens.

The optical path coupler couples and decouples a light projection optical path of illumination light and a light receiving optical path of fundus reflection light. The objective lens is disposed on a common optical path of the light projection optical path and the light receiving optical path, formed by the optical path coupler. In this case, it is preferable that the imaging optical axis and the optical axis of the objective lens match each other.

Various beam splitters may be used as the optical path coupler. In this case, the optical path coupler may be a perforated mirror, may be a simple mirror, may be a half mirror, or may be other beam splitters.

The light projection and reception separating unit separates a light projection region and a light reception region on the pupil of the subject eye.

Figure 9:
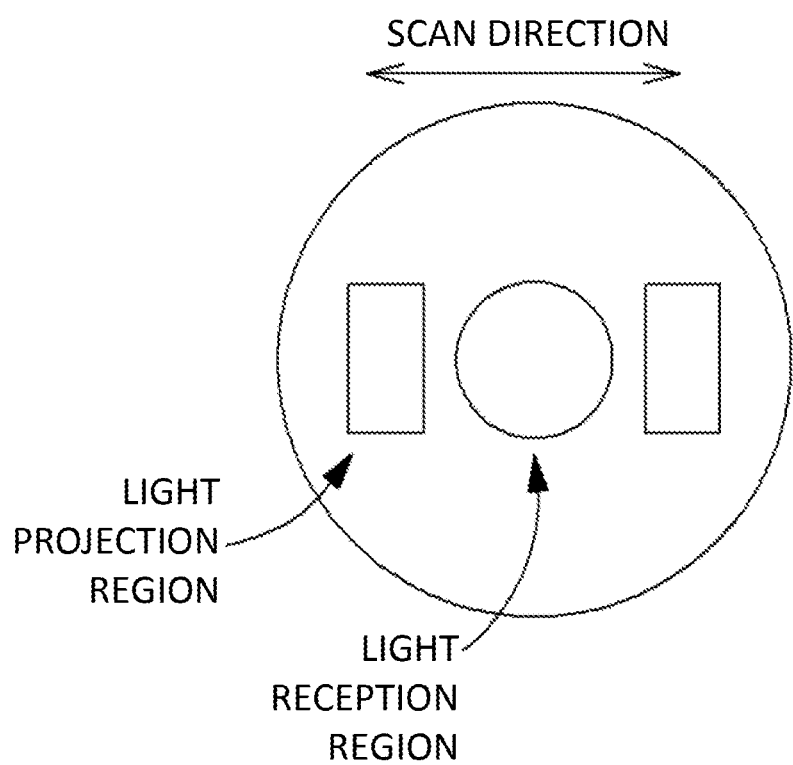
FIG. 9 is a diagram showing aspects of the irradiation and scan of the illumination light on the fundus in the optical system shown in FIG. 2.

In detail, as shown in FIGS. 2 and 9, the light projection region is formed at two positions separated from each other in a scanning direction of illumination light by the light projection and reception separating unit. The two light projection regions may be formed with the imaging optical axis being interposed therebetween. In the first embodiment, the light projection and reception separating unit may form at least two light projection regions, and may form three or more light projection regions. Illumination light that passes through each of the light projection regions irradiates the same slit-shaped region on the fundus. Along with the driving of the scanning unit, the slit-shaped region is scanned.

As shown in FIG. 9, the light projection and reception separating unit is formed to be interposed between two light projection regions by the light projection and reception separating unit. In other words, the respective regions are formed in one line in the order of one light projection region, a light reception region, and the other light projection region. Further, the light reception region may be formed on the imaging optical axis. The light projection region and the light reception region may be disposed so as not to overlap each other. In this case, it is possible to reduce occurrence of reflection and scattering of part of illumination light at the cornea and the intermediate light-transmitting member, and thus, occurrence of flare in the fundus image.

The light projection and reception separating unit may include a plurality of members that are respectively disposed on the light projection optical path of the illumination light and the light receiving optical path thereof.

The light projection and reception separating unit may be configured so that a part of the members set irradiation positions of the illumination light at least two positions spaced from each other in the scanning direction of the illumination light, on a pupil conjugate plane of the light projection optical path of the illumination light, for example. In this case, illumination light sources may be disposed at the two positions on the pupil conjugate plane, so that the irradiation positions may be set. Alternatively, openings through which the illumination light from the light sources passes may be respectively disposed at the two positions on the pupil conjugate plane as apparent illumination light sources, so that the irradiation positions may be set.

In other words, the light projection and reception separating unit may include at least two illumination light sources or two apparent illumination light sources, disposed at different positions in the scanning direction at a position that conjugates with the pupil of the subject eye. Accordingly, the light projection regions are formed at two positions separated from each other in the scanning direction of the illumination light. More preferably, two illumination light sources or two apparent illumination lighting sources may be symmetrically disposed with respect to the imaging optical axis. Thus, the two light projection regions may be symmetrically with respect to the imaging optical axis. A light projection state from two illumination light sources or two apparent illumination light sources may be controlled for each light source by the control unit (which will be described later). As a result of the control of the light projection state for each light source, whether to pass the illumination light therethrough is individually set with respect to each light projection region. The number of illumination light sources or the apparent illumination light sources included in the light projection and reception separating unit may be three or more.

As the light projection state, there may be at least two kinds of states, that is, a state where illumination light from the illumination light sources or the apparent illumination light sources reaches the subject eye, and a state where the illumination light from the illumination light sources or the apparent illumination light sources does not reach the subject eye. Change of the light projection state may be realized by a lighting control of the light source. Further, the light projection state may be changed using a shutter capable of selectively cutting off light beams from the illumination light sources or the apparent illumination light sources toward the subject eye.

Further, the light projection and reception separating unit may be configured so that a part thereof passes fundus reflection light through the light reception region that is a region sandwiched between two light projection regions toward the imaging plane side and does not pass other light toward the imaging plane side, on the pupil conjugate plane of the light receiving optical path of the illumination light. For example, the light projection and reception separating unit may include a light shielding member that passes the fundus reflection light through the light reception region toward the imaging plane and shields the other light. The light shielding member may be disposed on the pupil conjugate plane on the light receiving optical path, for example. For example, in a case where an aperture having an opening around the imaging optical axis as the light shielding member is provided, the light reception region is formed by an opening image of the aperture.

In a case where the light shielding member is included in the light projection and reception separating unit, the light shielding member may also be used as the above-described optical path coupler, or may be provided as a separate member from the optical path coupler.

<Fourth Artifact Suppressing Process>

In the above-described apparatus configuration, the control unit may set whether to pass illumination light, individually with respect to two light projection regions on the pupil of the subject eye. In this case, the control unit may capture a fundus image on the basis of illumination light that is selectively projected through (any) one of two light projection regions.

Figure 10A:
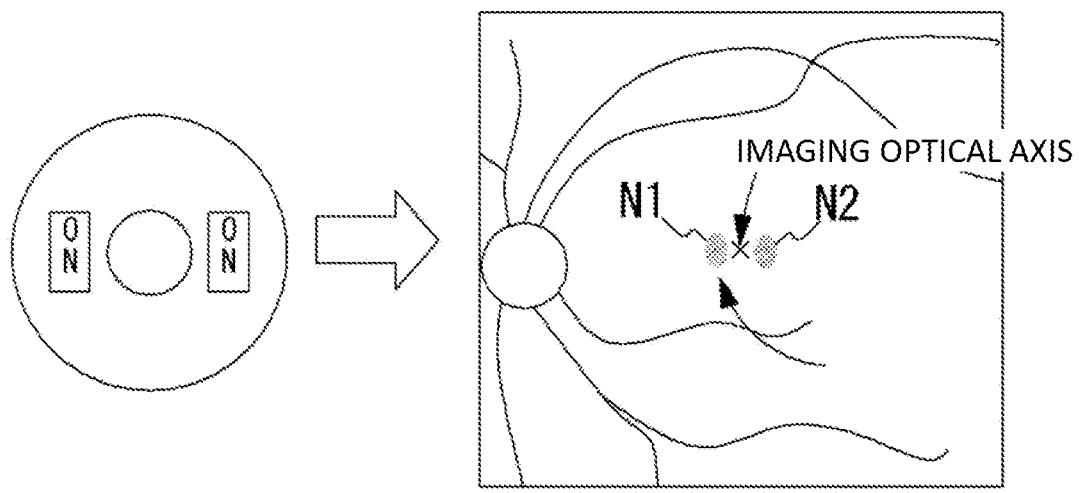
FIG. 10A is a diagram for explaining an outline of a fourth artifact suppressing process, which shows a fundus image obtained in a case where illumination light is emitted simultaneously through two light projection regions.

At a position in the vicinity of the imaging optical axis in the fundus image, there is a case where a reflection image (bright spot image, a kind of artifact) is generated due to reflection of the illumination light at a central portion of the lens surface of the objective lens. Since the light projection region is spaced away from the imaging optical axis, the reflection image easily appears at a position that slightly deviates from the position of the imaging optical axis in the fundus image. As an example, a fundus image captured by simultaneously projecting illumination light through both of two light projection regions is shown in FIG. 10A. As shown in FIG. 10A, reflection images (indicated by reference signs N1 and N2) may be generated at two locations with the imaging optical axis being interposed therebetween, at a central portion of the fundus image, corresponding to two light projection regions. The two reflection images appear along the scanning direction (in other words, at different positions in the scanning direction).

Figure 10B:
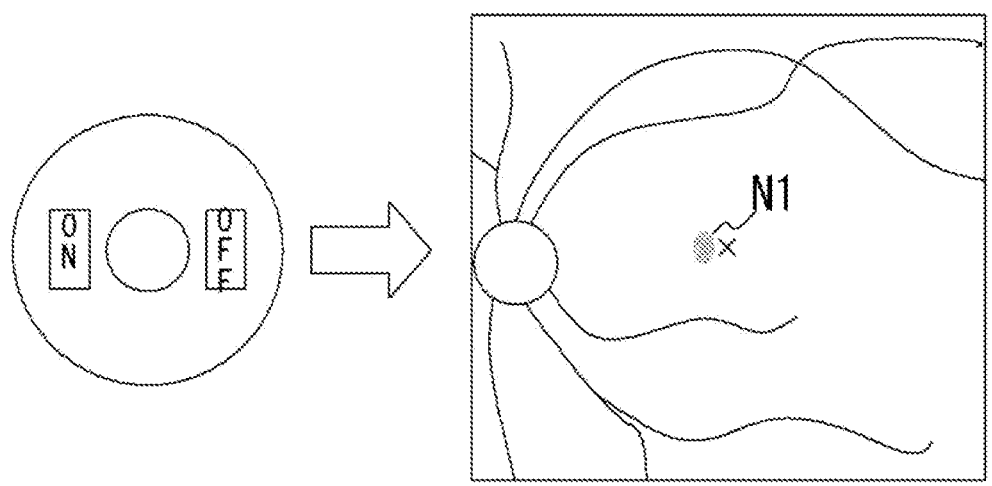
FIG. 10B is a diagram for explaining the outline of the fourth artifact suppressing process, which shows a fundus image obtained in a case where illumination light is selectively emitted through one of the two light projection regions.

In contrast, in this embodiment, the illumination light is selectively projected through one of two light projection regions to the fundus, and thus, a fundus image is captured. Thus, in the objective lens, locations where a reflection image is generated is reduced to the half, compared with the above-mentioned case. As a result, as shown in FIG. 10B, it is possible to reduce a reflection image in the fundus image to the half. As described above, since illumination light is selectively projected to the fundus through one of two light projection regions on the pupil of the subject eye to capture a fundus image, it is advantageous in reducing an artifact.

<Fifth Artifact Suppressing Process>

The control unit may selectively project illumination light to the fundus through one of two light projection regions to capture a first fundus image, and then, may change the light projection region to the other region where the illumination light is to be projected and may selectively project the illumination light through the other one to capture a second fundus image. With such two imaging operations, two fundus images of which occurrence positions of artifacts such as reflection images at the objective lens are different from each other depending on the light projection regions used for imaging are obtained. Between the first imaging and the second imaging, the imaging may be performed without changing a positional relationship between the subject eye and the imaging optical system. Further, it is preferable that the imaging of the second fundus image is consecutively and automatically performed from the imaging of the first fundus image.

In this embodiment, in capturing two fundus images, it is not necessary to change the positional relationship between the subject eye and the imaging optical system, and moreover, it is possible to change the light projection region on the pupil of the subject eye in a relatively short time, through lighting switching of the light source, driving of the shutter, or the like. Thus, it is possible to capture two fundus images in a short time. As a result, even in a case where the first fundus image and the second fundus image are consecutively captured, the burden of the examinee is suppressed. Further, even in a case where illumination light is visible light, since the second imaging is rapidly performed after the first imaging, it is possible to reduce the influence of miosis caused by the first imaging on the second imaging.

Here, as the influence of the miosis, for example, there is a phenomenon that illumination light and fundus reflection light are vignetting at the iris so that a fundus image becomes dark. The influence of the vignetting (change in brightness) between an image central portion and an image peripheral portion are not necessarily uniform. For example, in the image peripheral portion, as an imaging field angle becomes larger, the influence of the vignetting may easily become larger.

In the fifth artifact suppressing process, one fundus image (hereinafter, referred to as a "composite image") may be generated by combining these two fundus images. The combining process is executed by the image processing unit. In this embodiment, in order to obtain an image in which the influence of artifacts is suppressed, the combining process is performed. The combining method may employ various methods as described below, for example.

Figure 11:
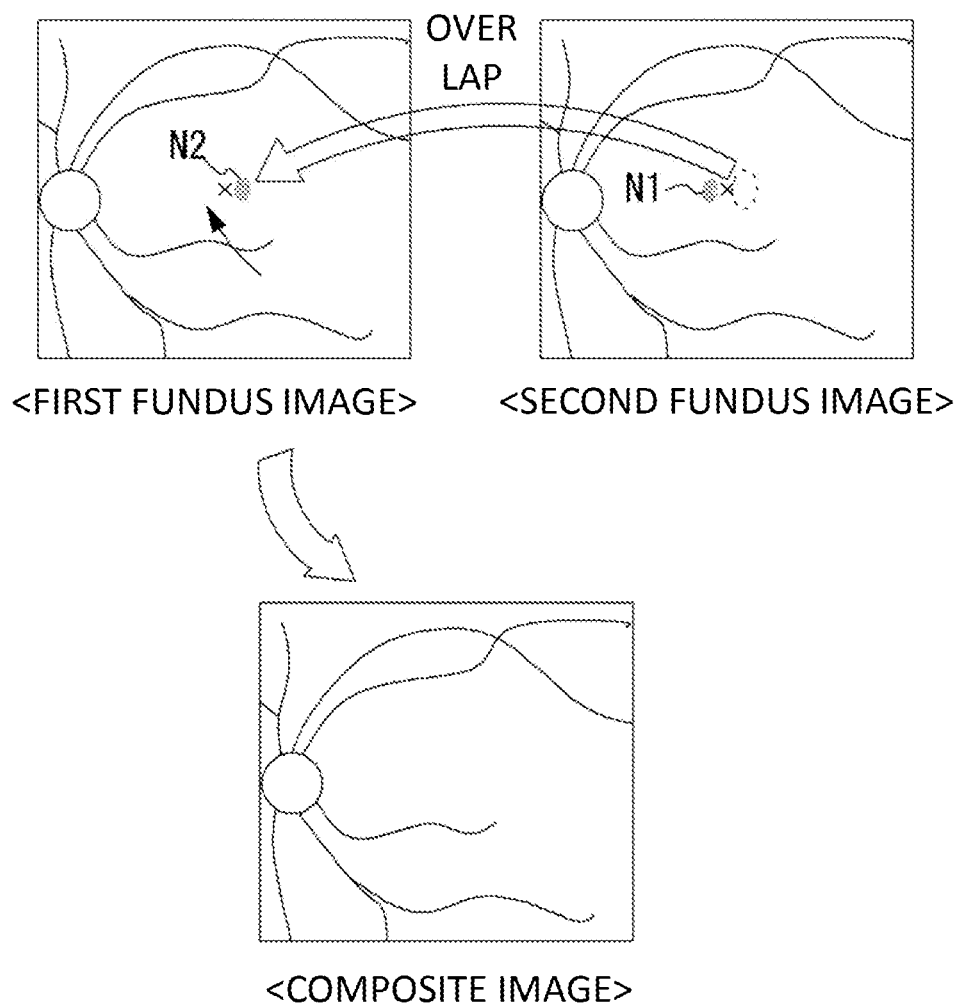
FIG. 11 is a diagram for explaining an outline of a fifth artifact suppressing process.

For example, by replacing a region including an artifact in one fundus image among two fundus images with a part of the other fundus image corresponding to the region, the composite image may be generated (see FIG. 11). Here, the replacement may be performed in the unit of a scan line. For example, in a case where the above-described reflection image is generated as an artifact, by replacing the reflection image generated at an image central portion of one fundus image with the corresponding region in the other fundus image, the composite image may be generated.

Further, the composite image may be generated as an averaged image of two fundus images. In this case, an averaging process may be performed by assigning different addition rates between the reflection image and a region other than the reflection image.

The region where the reflection image is generated has some fluctuation depending on the diopter, but becomes an approximately constant range with reference to the imaging optical axis. Accordingly, in two fundus images, a region to be combined with the other image in the combining process may be determined in advance. Here, the invention is not limited thereto, a reflection image detection process may be performed with respect to the fundus images, and the region to be combined may be individually set on the basis of the result of the detection process. Further, the region to be combined may be set in accordance with the diopter.

The control unit may capture the first fundus image on the basis of scan in only a part of a scan range corresponding to the composite image, may change the light projection region, may capture the second fundus image on the basis of scan in the remaining part of the scan range, and may combine (collage) the respective fundus images, to thereby generate the composite image. In this case, it is preferable that the scan range is divided into two sections around the imaging optical axis and the fundus images are respectively captured in the two divided scan ranges. In this case, the combining process is not necessarily limited to the image processing. For example, by changing the light projection region to which illumination light is projected at a timing when the illumination light arrives at a division position of the scan range, it is possible to form a composite image on the imaging plane.

In this case, between two fundus images, it is preferable that a relationship between the scan range on the fundus and the light projection region to which the illumination light is projected is a relationship in which the scan range and the light projection region cross each other between two fundus images. For example, in a case where two light projection regions are disposed in the vertical direction and the illumination light is scanned in the vertical direction on the fundus, when passing the illumination light through an upper light projection region, the first fundus image may be captured on the basis of scan of the lower half of the fundus, and when passing the illumination light through a lower light projection region, the second fundus image may be captured on the basis of scan of the upper half of the fundus, to thereby generate a composite image from both the fundus images. In this case, in relation to the respective light projection regions, images obtained by capturing portions that do not easily include an artifact such as a reflection image of the objective lens and flare are combined. Accordingly, it is possible to obtain a composite image in which artifacts are suppressed.

Instead of the combining process, the following imaging control may be performed. That is, the light projection region may be changed by the control unit at a timing when the illumination light for scanning the fundus during imaging arrives at a boundary position of two divided regions. Without the necessity of the combining process, a composite image in which a reflection image is suppressed is generated.

<Sixth Artifact Suppressing Process>

In the sixth artifact suppressing process, without changing the positional relationship between the imaging optical axis and the visual axis of the subject eye, the fundus image is captured twice ((at least twice). Between two imaging operations, the control unit changes imaging conditions other than the positional relationship. Thus, a first fundus image in which an artifact is suppressed and a second fundus image with image quality prioritized over the first fundus image are captured, and a corresponding region in the first fundus image is combined with a region including an artifact in the second fundus image. As a result, the apparatus acquires a composite image that is a fundus image in which artifacts are suppressed.

In the sixth artifact suppressing process, since the positional relationship between the imaging optical axis and the visual axis of the subject eye is not changed between two times of imaging, as compared with the second artifact suppressing process, it is possible to perform imaging twice in a shorter time to obtain a composite image.

Various conditions that there is a trade-off between image quality and difficulty in occurrence of artifacts may be obtained as imaging conditions changed between two times of imaging.

For example, between two times of imaging, the control unit may change an imaging condition relating to the diopter correction amount. In this case, the first fundus image may be, for example, a fundus image obtained by performing the artifact suppressing process in the above-described first embodiment. That is, the first fundus image may be a fundus image captured by adjusting the irradiation-side correction amount to a value different from the light receiving-side correction amount. In this case, the second fundus image may be a fundus image captured in a state where the irradiation-side correction amount and the light receiving-side correction amount match each other.

Further, for example, between two times of imaging, the control unit may change a condition relating to a separation state between fundus reflection light and harmful light. In this case, the first fundus image may be captured under an imaging condition such that the luminance becomes lower than that in the second fundus image.

For example, in capturing the first fundus image, the opening of the aperture that is disposed on at least one of the light projection optical system or the light receiving optical system may be reduced compared with the case of imaging the second fundus image. For example, in the above-described slit scan type optical system, the size of the light projection unit (for example, the opening) in the slit forming unit in the case of capturing the first fundus image may be reduced compared with the case of capturing the second fundus image. Further, a passing region of fundus reflection light in the harmful light removing unit (for example, the aperture) provided in the light receiving optical system may be limited in the case of capturing the first fundus image, compared with the case of capturing the second fundus image. Thus, harmful light due to reflection at the objective lens or the like is suitably separated from fundus reflection light that is guided to the imaging plane. As a result, it is possible to easily acquire a fundus image in which artifacts are suppressed.

In the case of the slit scan type optical system, one or both of the slit forming unit and the harmful light removing unit may be a variable slit. In the case of the variable slit, the width of an irradiation region or a valid region (imaging region), or the widths of both the regions may be changeable between a first width and a second width that is wider than the first width. In this case, one or both of the slit forming unit and the harmful light removing unit may have at least two kinds of slit openings, that is, a first slit opening corresponding to the first width and a second slit opening corresponding to the second width.

Figure 13:
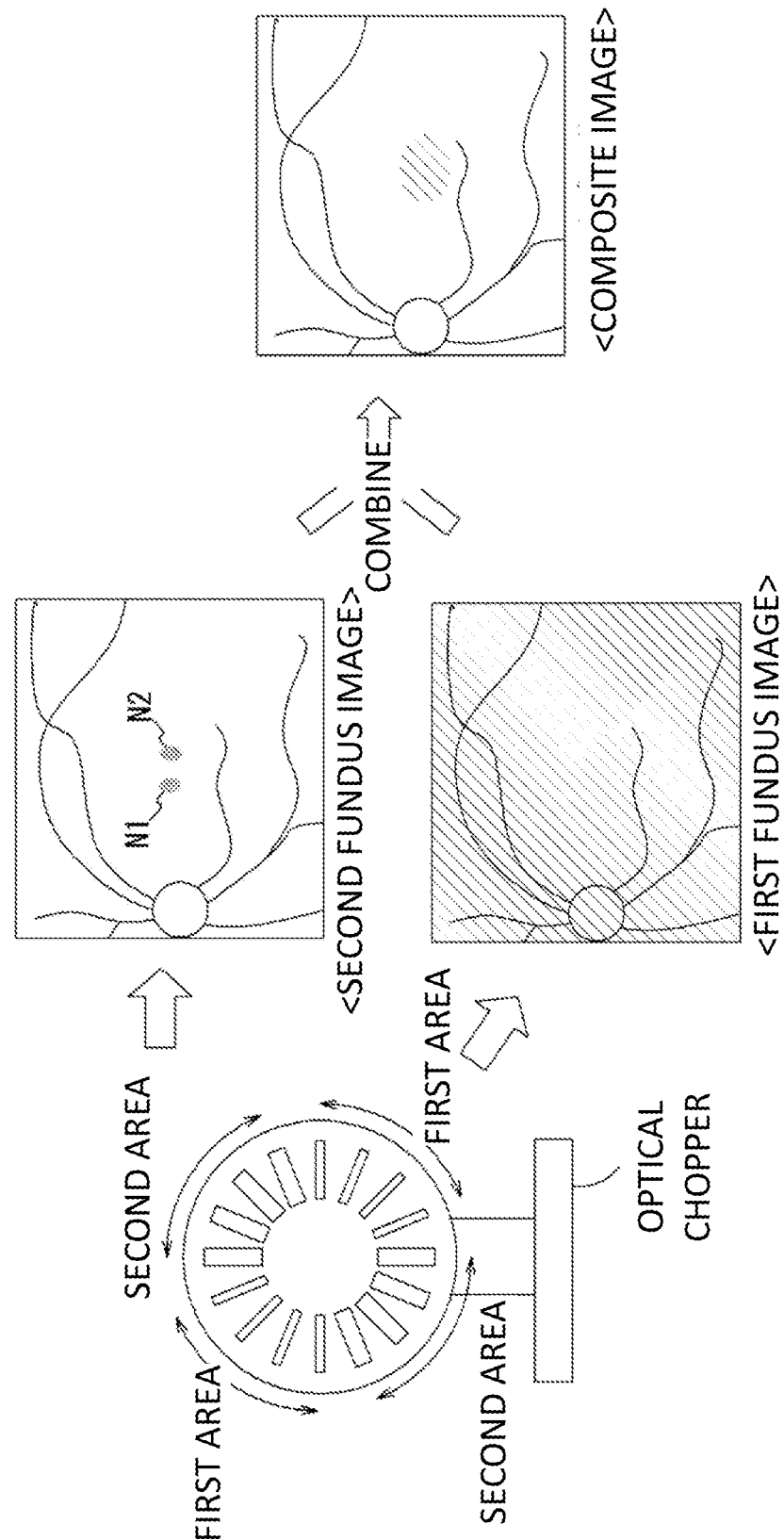
FIG. 13 is a diagram for explaining an outline of a sixth artifact suppressing process, which particularly shows an example in which an optical chopper in which slits having different widths are formed.

In this case, as shown in FIG. 13, the fundus imaging apparatus may include an optical chopper that is provided with a rotating body (for example, a wheel), as a scanning unit. In the optical chopper, a rotating body in which a plurality of slit openings are arranged side by side on one circumference corresponds to one or both of the slit forming unit and the harmful light removing unit. In the optical chopper, the rotating body is driven to be rotated. Thus, the plurality of slit openings are continuously transverse to an optical path of illumination light or return light. The shape of the rotating body, for example, may be a disc shape (wheel shape) as shown in FIG. 13, or may be a cylindrical shape. In the cylindrical-shaped rotating body, the plurality of slits are formed on a cylindrical side surface. The rotating body may be driven at a constant speed.

In the example of FIG. 13, the rotating body includes a first area where one or two or more first slit openings corresponding to the first width are continuously arranged, and a second area where one or two or more second slit openings corresponding to the second width are continuously arranged. In this case, in the control unit, between a first period during which the first area passes through the optical path and a second period during which the second area passes through the optical path, the width of the illumination region or the valid region (imaging region) on the fundus is changed. The control unit may acquire a fundus image obtained in the first period as a first fundus image, and may acquire a fundus image obtained in the second period as a second fundus image, to thereby generate a composite image of both the fundus images.

In a case where the illumination light is visible light, it is preferable to first capture the second fundus image of which the image quality is prioritized among the two fundus images, and then, to capture the first fundus image. Accordingly, the control unit may execute consecutive imaging operations of capturing two fundus images in a predetermined interval in the order of the second fundus image and the first fundus image (consecutive imaging process). It is preferable that the predetermined interval is a sufficiently short interval from a period of time (several tens of seconds) from imaging using the visible light to elimination of the miosis.

In a case where two fundus images are captured in a short time using the visible light, miosis occurs, and thus, in an image captured later, a peripheral portion easily becomes dark due to vignetting of the illumination light at the iris. On the other hand, the second fundus image of which the image quality is prioritized is captured earlier, and then, the first fundus image is captured, and thus, a fundus image in which a peripheral portion is also good in a composite image is easily obtained.

In a case where the scanning unit is the optical chopper, the apparatus may further include a sensor that detects a rotational position of the rotating body. On the basis of a signal from the sensor, exposure of an imaging element and sweeping of an image may be controlled.

Third Embodiment

Next, a third embodiment will be described. A fundus imaging apparatus according to the third embodiment (see FIG. 14) scans the fundus by slit-shaped illumination light, to thereby capture a fundus image. An apparatus according to the third embodiment captures a fundus image in a state where an aperture is disposed at a position different from a fundus conjugate position. During imaging, as the aperture is disposed at the position different from the fundus conjugate position, an artifact due to reflection at the objective lens can be suppressed. The fundus imaging apparatus according to the third embodiment may include a part of the plurality of embodiments described above in the first embodiment.

The fundus imaging apparatus according to the third embodiment includes at least an imaging optical system and a diopter correction optical system. Additionally, the fundus imaging apparatus may include a control unit.

The imaging optical system according to the third embodiment includes an irradiation optical system, a light receiving optical system, and a scanning unit. The irradiation optical system irradiates the fundus of a subject eye with slit-shaped illumination light through the objective lens. The light receiving optical system shares the objective lens with the irradiation optical system. The light receiving optical system forms a fundus image based on fundus reflection light of the illumination light on an imaging plane.

The scanning unit according to the third embodiment is used to displace one or both of a local illumination region and a local imaging region that correspond to parts of an imaging range of the fundus. The scanning unit according to the third embodiment may include at least a slit and a drive unit (driver). Alternatively, the scanning unit may be a device that scans illumination light formed like a slit shape in advance. The aperture may be disposed on any one of the irradiation optical system and the light receiving optical system, or may be disposed on both the optical systems. The shape of an opening in the aperture may be a slit shape (see the first and second embodiments), may be a circular shape, or may be other shapes, for example. Further, in a case where the device that scans the illumination light formed in the slit shape in advance is used as the scanning unit, the aperture may be statically positioned with respect to the optical systems.

The diopter correction optical system corrects a diopter at the imaging optical system.

In the third embodiment, in the above-described apparatus configuration, the fundus image is captured in a state where the aperture is disposed at the position different from the fundus conjugate position. Here, the aperture may be used to remove stray light from an anterior eye segment. In other words, the aperture is in a non-conjugate positional relationship with either of the cornea or the crystalline lens. Further, it is preferable that the aperture is disposed in the vicinity of the fundus conjugate position within a range where the suppression effect of the reflection from the objective lens is enjoyable.

In this case, the aperture may be disposed in advance at a position separated from both of the imaging plane and its conjugate position, for example. Here, it is preferable that the aperture is disposed on a positive diopter side with reference to the conjugate position of the imaging plane. As the aperture is disposed in advance at the position different from both of the imaging plane and its conjugate position, it is possible to distance the position of the aperture from a condensing position of reflection light at the objective lens, and thus, to suppress an artifact.

Further, in a case where the aperture is disposed at the position separated from both of the imaging plane and its conjugate position, in a state where diopter correction in both of the irradiation optical system and the light receiving optical system is performed without excess or deficiency with respect to the refractive power of the subject eye, the fundus image may be captured. In this case, the diopter correction optical system may not necessarily adjust independently the irradiation-side correction amount (the diopter correction amount in the irradiation optical system) and the light receiving-side diopter correction amount (the diopter correction amount in the light receiving optical system). Therefore, it is possible to easily simplify the apparatus configuration.

On the other hand, the fundus imaging apparatus according to the third embodiment may include the same diopter correction optical system as in the first embodiment. In this case, the diopter correction optical system may independently adjust the irradiation-side correction amount that is the diopter correction amount in the irradiation optical system and the light receiving-side correction amount that is the diopter correction amount in the light receiving optical system, respectively. In capturing the fundus image, the control unit may control the diopter correction optical system, and may set the irradiation-side correction amount and the light receiving-side correction amount to different values. Here, the light receiving-side correction amount may be a value depending on the refractive power of the subject eye, and the irradiation-side correction amount may be a value different from the value depending on the refractive power of the subject eye.

FIRST EXAMPLE

Next, an example of the fundus imaging apparatus according to the first to third embodiments will be described with reference to FIGS. 1 to 4B, FIG. 12, and FIG. 15.

The fundus imaging apparatus 1 (hereinafter, simply referred to as an "imaging apparatus 1") forms illumination light in a slit shape on the fundus of a subject eye, scans a region formed in the slit shape on the fundus, and receives fundus reflection light of the illumination light, to thereby capture a front image of the fundus.

<Appearance of Apparatus>

An external configuration of the imaging apparatus 1 will be described with reference to FIG. 1. The imaging apparatus 1 includes an imaging unit 3. The imaging unit 3 mainly includes an optical system shown in FIG. 2. The imaging apparatus 1 includes a base 7, a drive unit 8, a face support unit 9, and a face imaging camera 110, and adjusts a positional relationship between a subject eye F and the imaging unit 3 using the above-mentioned units.

The drive unit 8 may move in a lateral direction (X direction) and a longitudinal direction (Z direction, in other words, an operation distance direction) with respect to the base 7. Further, the drive unit 8 further moves the imaging unit 3 in three-dimensional directions with respect to the subject eye E on the drive unit 8. The drive unit 8 is provided with an actuator for moving the drive unit 8 or the imaging unit 3 in predetermined respective movable directions, and is operated based on a control signal from the control unit 80. The face support unit 9 supports the face of the subject. The face support unit 9 is fixed to the base 7.

The face imaging camera 110 is fixed to a housing 6 so that a positional relationship with respect to the imaging unit 3 is constant. The face imaging camera 110 images the face of the subject. The control unit 100 specifies the position of the subject eye E from a captured face image, and controls the operation of the drive unit 8 to position the imaging unit 3 with respect to the specified position of the subject eye E.

The imaging apparatus 1 further includes a monitor 120. On the monitor 120, a fundus observation image, a fundus capturing image, an anterior eye segment observation image, or the like is displayed.

<Optical System of Example>

Next, an optical system of the imaging apparatus 1 will be described with reference to FIG. 2. The imaging apparatus 1 includes an imaging optical system 10 (fundus imaging optical system), and an anterior eye segment observation optical system 40. The optical systems are provided in the imaging unit 3.

In FIG. 2, a position that conjugates with the pupil of the subject eye is indicated by "Δ" on the imaging optical axis, and a fundus conjugate position is indicated by "X" on the imaging optical axis, respectively.

The imaging optical system 10 includes an irradiation optical system 10a and a light receiving optical system 10b. In this example, the irradiation optical system 10a includes a light source unit 11, a lens 13, a slit-shaped member 15a, lenses 17a and 17, a mirror 18, a perforated mirror 20, and an objective lens 22. The light receiving optical system 10b includes the objective lens 22, the perforated mirror 20, lenses 25a and 25b, a slit-shaped member 15b, and an imaging element 28. The perforated mirror 20 is an optical path coupler that couples optical paths of the irradiation optical system 10a and the light receiving optical system 10b. The perforated mirror 20 causes illumination light from the light source to be reflected toward the subject eye F, and passes part of fundus reflection light from the subject eye E, which passes through an opening, toward the imaging element. Various beam splitters may be used instead of the perforated mirror 20. For example, instead of the perforated mirror 20, a mirror in which a light transmitting portion and a light reflecting portion are reversed compared with the perforated mirror 20 may be used as the optical path coupler. In this case, an independent optical path of the light receiving optical system 10b is placed on a reflection side of the mirror, and an independent optical path of the irradiation optical system 10a is placed on a light transmitting side of the mirror. Further, the perforated mirror and the mirror that is its alternative means may be replaced with a combination of a half mirror and a light shielding mirror, respectively.

In this example, the light source unit 11 includes a plurality of types of light sources having different wavelength bands. For example, the light source unit 11 includes visible light sources 11a and 11b, and infrared light sources 11c and 11d. In this way, in the light source unit 11 of this example, two light sources are provided for each wavelength. Two light sources of the same wavelength are disposed to be spaced from an imaging optical axis L on a pupil conjugate plane. Two light sources are disposed along the X direction that is the scanning direction in FIG. 2, and are disposed in axial symmetry with respect to the imaging optical axis L. As shown in FIG. 2, an outer peripheral shape of two light sources may be a rectangular shape in which a length in a direction that intersects the scanning direction is longer than a length in the scanning direction.

Light from two light sources passes through the lens 13, and is then emitted to the slit-shaped member 15. In this example, the slit-shaped member 15a has a light transmitting portion (opening) that is elongated along the Y direction. Thus, on the fundus conjugate plane, the illumination light is formed in a slit shape (a region illuminated in a slit shape on the fundus is indicated by a reference sign B).

In FIG. 2, the slit-shaped member 15a is displaced by the drive unit 15c so that the light transmitting portion crosses the imaging optical axis L in the X direction. Accordingly, the scan of the illumination light in this example is realized. In this example, on the light receiving system side, similarly, the scan is performed by the slit-shaped member 15b. In this example, the slit-shaped members 15a and 15b on the light transmitting side and the light receiving-side are driven in conjunction with each other by one drive unit (actuator). In this example, the scanning unit is realized by the slit-shaped members 15a and 15b, and a drive unit (not shown).

In the irradiation optical system 10a, an image of each light source is relayed by an optical system from the lens 13 to the objective lens 22 to be formed on the pupil conjugate plane. In other words, on the pupil conjugate plane, images of two light sources are formed at separated positions in the scanning direction. In this way, in this example, two light projection regions P1 and P2 on the pupil conjugate plane are formed as images of two light sources.

Further, slit-shaped light that passes through the slit-shaped member 15a is relayed by an optical system from the lens 17a to the objective lens 22 to be image-formed on fundus Er. Thus, the illumination light is formed in a slit shape on the fundus Er. The illumination light is reflected on the fundus Er, and is extracted from the pupil Ep.

Here, since the opening of the perforated mirror 20 conjugates with the pupil of the subject eye, the fundus reflection light to be used for capturing a fundus image is limited to part thereof that passes through an image (pupil image) of the opening of the perforated mirror on the pupil of the subject eye. Thus, the image of the opening on the pupil of the subject eye becomes a light reception region R in this example. The light reception region R is formed to be interposed between two light projection regions P1 and P2 (images of two light sources). Further, as a result of appropriate setting of an imaging magnification of each image, the diameter of the opening, and an arrangement interval of two light sources, the light reception region R and two light projection regions P1 and P2 are formed so as not to overlap each other on the pupil. Thus, the occurrence of flare is satisfactorily reduced.

The fundus reflection light which has passed through the objective lens 22 and the opening of the perforated mirror 20 image-forms a slit-shaped region of the fundus Er at the fundus conjugate position through the lenses 25a and 25b. Here, as the light transmitting portion of the slit-shaped member 15b is disposed at an image forming position, harmful light is removed.

The imaging element 28 is disposed at the fundus conjugate position. In this example, the relay system 27 is provided between the slit-shaped member 15b and the imaging element 28, and thus, both the slit-shaped member 15b and the imaging element 28 are disposed at the fundus conjugate position. As a result, both removal of harmful light and image formation are satisfactorily performed. Alternatively, the relay system 27 may not be provided between the imaging element 28 and the slit-shaped member 15b, and both the imaging element 28 and the slit-shaped member 15b may be disposed to be close to each other. In this example, as the imaging element 28, a device having a two-dimensional light reception region may be used. For example, a CMOS, a two-dimensional CCD, or the like may be used. In the imaging element 28, an image of the slit-shaped region of the fundus Er, formed by the light transmitting portion of the slit-shaped member 15b, is projected. The imaging element 28 has a sensitivity to both infrared light and visible light.

In this example, as slit-shaped illumination light is scanned on the fundus Er, images (slit-shaped images) of scan positions on the fundus Er are sequentially projected for each scan line of the imaging element 28. Thus, an entire image of the scan range is projected in a time-division manner onto the imaging element. As a result, as the entire image of the scan range, a front image of the fundus Er is captured.

The scanning unit in the light receiving system in this example is a device that mechanically scans a slit, but the invention is not limited thereto. For example, the scanning unit on the light receiving optical system side may be a device that electronically scans the slit. As an example, in a case where the imaging element 28 is the CMOS, the scan of the slit may be realized by a rolling shutter function of the CMOS. In this case, by displacing a region to be exposed on the imaging plane in synchronization with the scanning unit in the projection system, it is possible to efficiently perform imaging while removing harmful light. Further, a liquid crystal shutter or the like may also be used as a scanning unit that electronically scans the slit.

The imaging optical system 10 has a diopter correction unit. In this example, diopter correction units (diopter correction optical systems 17 and 25) are respectively provided on an independent optical path of the irradiation optical system 10a and an independent optical path of the light receiving optical system 10b. Hereinafter, for ease of description, a diopter correction optical system on an irradiation side is referred to as the irradiation-side diopter correction optical system 17, and a diopter correction optical system on a light receiving-side is referred to as the light receiving-side diopter correction optical system 25. The irradiation-side diopter correction optical system 17 of this example includes lenses 17a and 17b, and a drive unit 17c (see FIG. 3). Further, the light receiving-side diopter correction optical system 25 of this example includes lenses 25a and 25b, and a drive unit 25c (see FIG. 3). A distance between the lens 17a and the lens 17b is changed in the irradiation-side diopter correction optical system 17, and a distance between the lens 25a and the lens 25b is changed in the light receiving-side diopter correction optical system 25. Thus, diopter correction is performed in each of the irradiation optical system 10a and the light receiving optical system 10b.

The drive unit 17c of the irradiation optical system 10a, and the drive unit 25c of the light receiving optical system 10b may be independently driven. As a result, in this example, as shown in FIG. 4B, an irradiation-side correction amount that is a diopter correction amount in the irradiation optical system 10a and a light receiving-side correction amount that is a diopter correction amount in the light receiving optical system 10b may be independently set.

In this example, each of the irradiation-side diopter correction optical system 17 and the light receiving-side diopter correction optical system 25 includes a telecentric optical system. Each telecentric optical system maintains the height of an image in an image side region even in a case where the diopter correction amount is changed. Thus, it is possible to maintain constantly a positional relationship between a slit opening of the irradiation optical system on the fundus and a slit opening of the light receiving optical system, regardless of the balance between the irradiation-side correction amount and the light receiving-side correction amount. Accordingly, it is possible to cause the slit opening of the irradiation optical system and the slit opening of the light receiving optical system on the fundus to constantly match each other, regardless of the balance between the irradiation-side correction amount and the light receiving-side correction amount. Further, it is possible to suppress a change in an image size due to a change in a diopter correction amount.

As shown in FIG. 2, the imaging optical system 10 includes a split index projecting optical system 50, as an example of a focus index projecting optical system. The split index projecting optical system 50 projects two split indexes onto the fundus. The split indexes are used for detecting a focusing state. Further, in this example, the refractive power of the subject eye E is acquired from a detection result of the focusing state.

The split index projecting optical system 50 may include at least a light source 51 (infrared light source), an index board 52, and a deflecting prism 53, for example. In this example, the index board 52 is disposed at a position corresponding to the imaging plane in the light receiving optical system 50. Similarly, each of the slit-shaped members 15a and 15b is disposed at a corresponding position. Specifically, in a case where the diopter correction amounts on the irradiation side and the light receiving-side are 0D, the index board 52 is disposed at a position that approximately conjugates with the fundus of emmetropia (0D eye). The deflecting prism 53 is disposed to be close to the index board 52 on the subject eye side with reference to the index board 52.

The index board 52 forms slit light as an index, for example. The deflecting prism 53 separates an index light beam through the index board 52 to form split indexes. The separated split indexes are projected onto the fundus of the subject eye through the irradiation-side diopter correction optical system 17 and the objective lens 22. Accordingly, the split indexes are background-reflected on the fundus image (for example, a fundus observation image).

In a case where the index board 52 deviates from the fundus conjugate position, two split indexes are separated on the fundus, and in a case where the index board 52 is disposed at the fundus conjugate position, two split indexes match each other. The conjugate relationship is adjusted by the irradiation-side diopter correction optical system 17 disposed between the deflecting prism 53 and the subject eye Er. Accordingly, in this example, defocusing is performed while causing the irradiation-side diopter correction amount and the light receiving-side diopter correction amount to match each other. Here, a separation state of the split indexes represents a focusing state. As the diopter correction amounts on the irradiation side and the light receiving-side are respectively adjusted so that two split indexes match each other, the imaging plane and each of the slit-shaped members 15a and 15b enters a positional relationship of conjugating with the fundus.

It is possible to derive the refractive power of the subject eye E from a diopter correction amount in a case where the imaging plane and each of the slit-shaped members 15a and 15b is in the positional relationship of conjugating with the fundus. Accordingly, in this example, an encoder (not shown) that reads out any one of the interval between the lens 17a and the lens 17b or the interval between the lens 25a and the lens 25b may be further provided, and the refractive power of the subject eye E may be acquired on the basis of a signal from the encoder.

Figure 12:
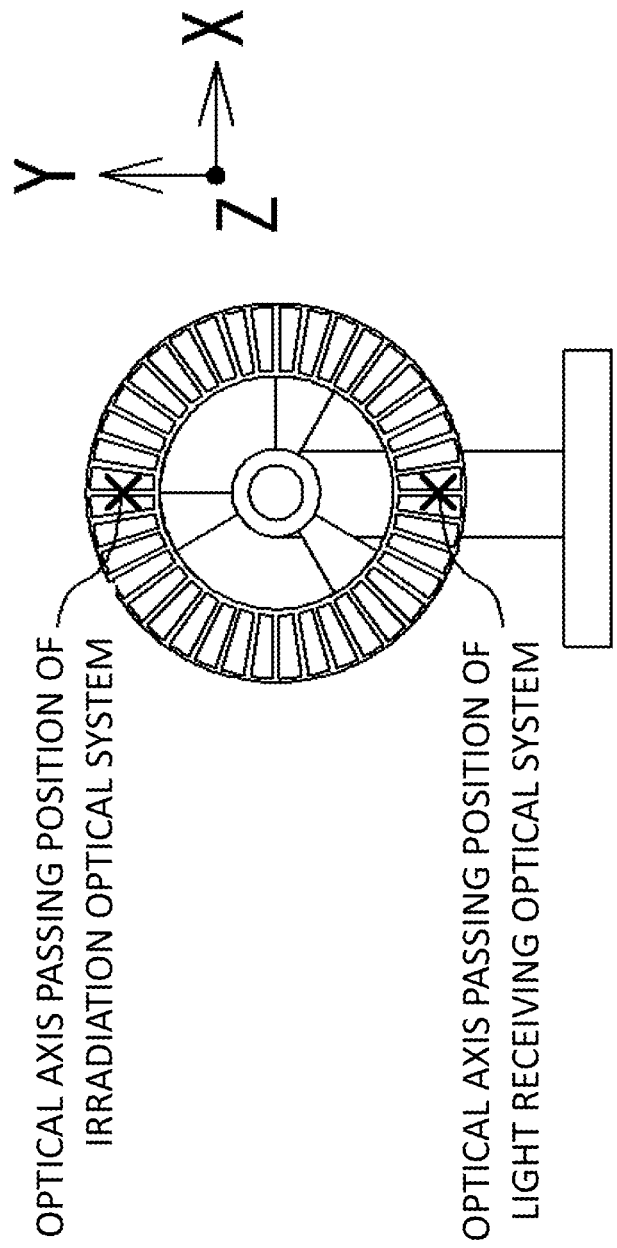
FIG. 12 is a diagram showing an optical chopper capable of being applied as a scanning unit in the optical system shown in FIG. 2.

The scanning unit may be an optical chopper as shown in FIG. 12, for example. The optical chopper has a wheel in which a plurality of slits are formed on the outer periphery thereof, and is able to scan the slits at high speed by rotating the wheel.

Here, in FIG. 2, the components from the light source unit 11 to the mirror 18 of the irradiation optical system 10a and the components from the perforated mirror 20 to the imaging element 28 of the light receiving optical system 10b are arranged in parallel in the X direction, but for example, by rotating the orientation of the perforated mirror 20 and the mirror 18 by 90° from the state shown in the figure to arrange both of the components in parallel in the Y direction, it is possible to apply the optical chopper as a scanning unit. In this case, as shown in FIG. 12, by causing an optical axis of the irradiation optical system 10a and an optical axis of the light receiving optical system 10b to be crossed in two places at an upper end and a lower end of the wheel, respectively, it is possible to easily synchronize scans of the light projection system and the light receiving system using one optical chopper.

<Anterior Eye Segment Observation Optical System>

Next, the anterior eye segment observation optical system 40 will be described. The anterior eye segment observation optical system 40 shares the objective lens 22 and the dichroic mirror 43 with the imaging optical system 10. The anterior eye segment observation optical system 40 further includes a light source 41, a half mirror 45, an imaging element 47, and the like. The imaging element 47 is a two-dimensional imaging element, and for example, is disposed at a position that optically conjugates with the pupil Ep. The anterior eye segment observation optical system 40 illuminates the anterior eye segment with infrared light to capture a front image of the anterior eye segment.

The anterior eye segment observation optical system 40 shown in FIG. 2 is only an example, and may image the anterior eye segment on an optical path that is independent of the other optical systems.

<Control System of First Example>

Figure 3:
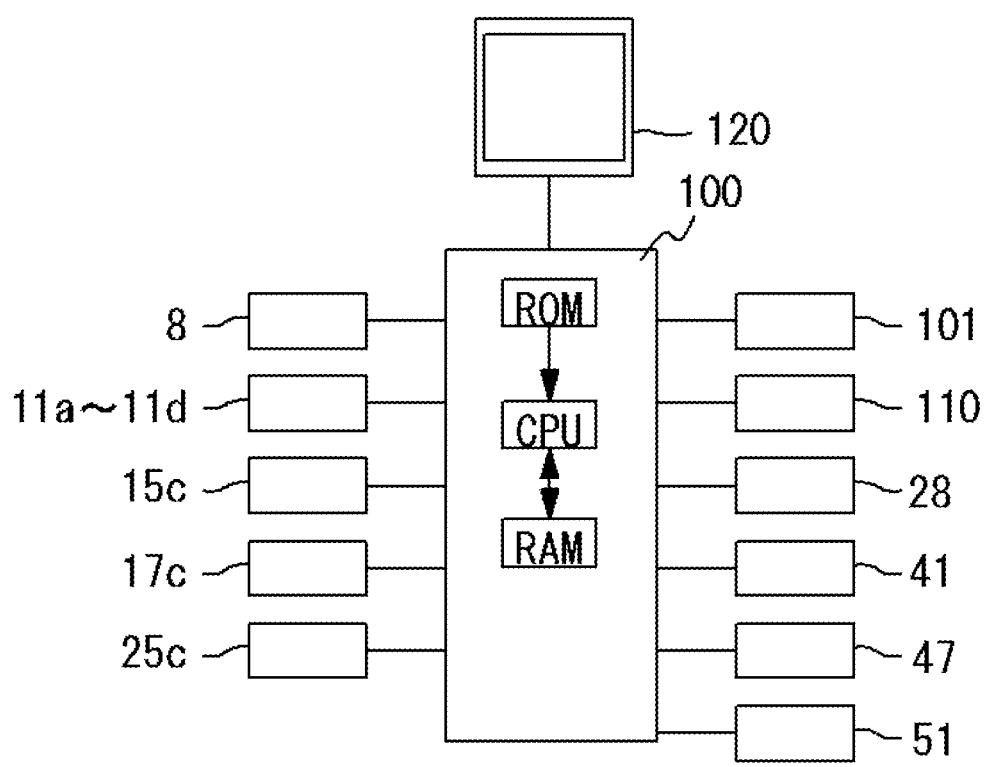
FIG. 3 is a block diagram showing a control system of the apparatus according to the first example.

Next, a control system of the imaging apparatus 1 will be described with reference to FIG. 3. In this example, the control unit 100 controls the respective units of the imaging apparatus 1. For convenience, it is assumed that image processing of a variety of images obtained by the imaging apparatus 1 is performed by the control unit 100. In other words, in this example, the control unit 100 also serves as an image processing unit.

The control unit 100 is a processing unit (processor) having an electronic circuit that performs a controlling process of each unit and a calculating process. The control unit 100 is realized by a central processing unit (CPU), a memory, and the like. The control unit 100 is electrically connected to a storage unit 101 through a bus or the like.

The storage unit 101 stores a variety of control programs, fixed data, and the like. Further, the storage unit 101 may store temporary data, or the like.

An image captured by the imaging apparatus 1 may be stored in the storage unit 101. Here, the invention is not necessarily limited thereto, and the captured image may be stored in an external storage device (for example, a storage device connected to the control unit 100 through LAN and WAN).

Further, the control unit 100 is also electrically connected to the respective units such as the drive unit 8, the light sources 11a to 11d, the drive unit 15c, the drive unit 17c, the drive unit 25c, the imaging element 28, the light source 41, the imaging element 47, the light source 51, the input interface 110, the monitor 120, and the like.

Furthermore, the control unit 100 controls the above-described respective members on the basis of an operation signal output from an input interface 110 (operation input unit). The input interface 110 is an operation input unit that receives an operation of an examiner. For example, the input interface 110 may be a mouse, a keyboard, or the like.

<Operation of First Example>

Figure 15:
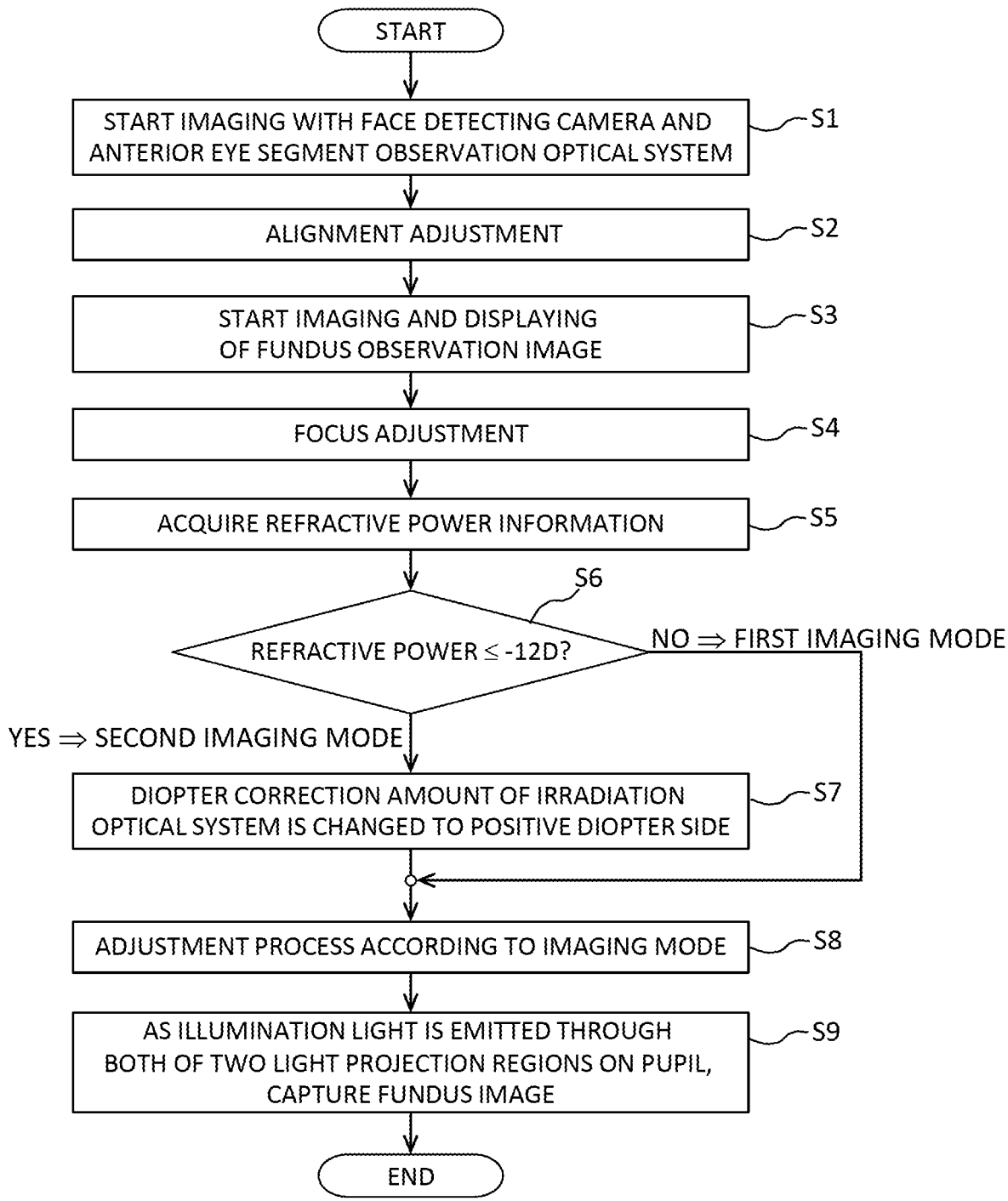
FIG. 15 is a flowchart showing an imaging operation of the apparatus.

Next, an imaging operation will be described with reference to a flowchart of FIG. 15.

In the imaging apparatus 1, as the face of a subject is placed against a face support unit 9 and is included in an imaging range of a face detecting camera 110, the imaging operation may be automatically started.

First, imaging operations with the face detecting camera 110 and the anterior eye segment observation optical system 40 are performed in parallel (S1), and alignment adjustment is performed using both the imaging results (S2).

Specifically, the control unit 100 detects a position of one of the right and left eyes included in a face image, and drives the drive unit 8 on the basis of position information thereof. Thus, the position of the imaging unit 4 is adjusted up to a position where anterior eye segment observation is possible.

Then, an alignment reference position is set on the basis of an anterior eye segment front image, and an alignment with respect to the set alignment reference position is guided. In this example, a positional relationship between the subject eye E and the imaging unit 3 is adjusted by the control unit 100 on the basis of the anterior eye segment front image. In this example, in the control unit 100, a first reference position for targeting a positional relationship in which a pupil center and an image center (in this example, the position of the imaging optical axis L) in the anterior eye segment observation image approximately match each other is set on the basis of a signal from the imaging element 47. Further, misalignment from the first reference position is detected, and the imaging unit 4 is moved in vertical and horizontal directions in a direction where the misalignment is eliminated. Here, for example, the misalignment from the first reference position may be detected on the basis of the amount of deviation between the pupil center and the imaging optical axis on the anterior eye segment observation image. Further, in a case where the fundus imaging apparatus 1 includes an alignment projection optical system that projects an alignment index to the cornea vertices, for example, misalignment may be detected on the basis of the amount of deviation between the alignment index and the imaging optical axis.

Further, the control unit 100 moves the imaging unit 4 in the front-rear direction to fit the focus of the anterior eye segment observation image to the pupil Ep. Thus, a distance to the subject eye from the apparatus is adjusted to a predetermined operation distance.

Thus, in this example, as a result of the alignment adjustment of S2, the positional relationship between the subject eye and the imaging unit 4 is adjusted to a position (first reference position in this example) such that the center of the light reception region R on the pupil of the subject eye (that is, the imaging optical axis) matches the pupil center.

After a first imaging mode is set, the control unit 100 starts imaging and displaying of the fundus observation image (S3). Specifically, the control unit 100 simultaneously turns on the light sources 11c and 11d, starts driving of the drive unit 15c, and repeatedly scans slit-shaped illumination light in a predetermined range on the fundus Er. For a predetermined number of scans (at least once), a fundus image that is captured in approximately real time is generated from time to time as a fundus observation image on the basis of a signal output from the imaging element 28. The control unit 100 may display the fundus observation image on the monitor 120 as an approximately real-time video image.

Then, on the basis of the fundus observation image, a focusing state in the irradiation optical system and the light receiving optical system is adjusted (S4). In this example, after the alignment is completed, the diopter correction optical system is driven to perform focus adjustment. Here, in this example, both the irradiation-side diopter correction optical system 17 and the light receiving-side diopter correction optical system 25 are driven.

In the focus adjusting process, the control unit 100 first turns on the light source 51 to start projection of a split index with respect to the fundus. The control unit 100 performs defocus by changing a correction amount while making the irradiation-side diopter correction amount and the light receiving-side diopter correction amount match each other. Furthermore, the control unit 100 detects a separation state of split indexes from the fundus observation image every time when the correction amount is changed, and adjusts the irradiation-side diopter correction amount and the light receiving-side diopter correction amount until the split indexes match each other. As a result of the adjustment, the imaging plane and each of the slit-shaped members 15a and 15b enters a positional relationship of conjugating with the fundus.

Further, in this example, the diopter correction amount in a case where the split indexes match each other is acquired as refractive power information by the control unit 100 (S5).

Then, the control unit 100 sets the imaging mode on the basis of the refractive power information. First, the diopter correction amount that is the refractive power information is compared with a predetermined threshold (S6). In this example, on the assumption that an artifact occurs in a case where each of the irradiation-side correction amount and the light receiving-side correction amount is on a negative diopter side with reference to −12D, "−12D" is employed as a refractive power threshold. That is, the first range indicated by the reference sign A1 in FIG. 4B is a range on a positive diopter side with reference to "−12D" in this example. Further, the second range indicated by the reference numeral A2 is "−12D" in this example, and in a range on a negative diopter side with reference to "−12D". Here, since a diopter range in which an artifact occurs due the reflection on the objective lens 22 is changed depending on an optical design of the apparatus, a value depending on the optical design of the apparatus may be employed as a threshold.

In this example, in a case where the refractive power of the subject eye is a value on the positive diopter side with reference to "−12D", the first imaging mode is set (S6: No). On the other hand, in a case where the refractive power of the subject eye is "−12D" or a value on the negative diopter side with reference to "−12D", the second imaging mode is set (S6: Yes). The first imaging mode is an invalid mode in this example, and the second imaging mode is a valid mode in this example.

In the first imaging mode, the procedure proceeds to a process of S8, and the imaging conditions other than the diopter correction amount are adjusted according to the imaging mode (S8). After adjustment, a fundus image is captured (S9). Here, light emission from the light sources 11c and 11d for observation is stopped, and then, the light sources 11a and 11b for imaging may be turned on. In this case, a fundus image based on visible light emitted from the light sources 11a and 11b is acquired as a result of imaging.

In this example, in the first imaging mode, in a state where the irradiation-side correction amount and the light receiving-side correction amount match each other, the fundus image is captured (see FIG. 4A). During imaging, the irradiation-side correction amount and the light receiving-side correction amount become values immediately after the adjustment in the focus adjusting process (S5). Accordingly, the fundus is imaged in a state where the diopter correction amount is in a range where an artifact does not cause a problem and the imaging plane and each of the slit-shaped members 15*a* and 15*b* are in the positional relationship of conjugating with the fundus. Therefore, a good fundus image is captured.

On the other hand, in the second imaging mode, the irradiation-side correction amount is changed to the positive diopter side with respect to a value in a case where the split indexes match each other (see FIG. 4B). Thus, since the condensing position of illumination light becomes distant from the objective lens, an artifact due to the reflection of the objective lens 22 does not easily occur. In this example, a value of the irradiation-side correction amount after the change may be a fixed value, or may be varied depending on the light receiving-side correction amount within a range where the irradiation-side correction amount does not match the light receiving-side correction amount. In this example, the irradiation-side correction amount is changed to "−10D" that is a value on the positive diopter side with respect to the threshold. However, the invention is not necessarily limited thereto, and the irradiation-side correction amount may be changed to the threshold.

Then, the imaging conditions other than the diopter correction amount are adjusted according to the second imaging mode. Here, since the diopter correction amount in the irradiation optical system deviates from the best focus, slit light emitted as illumination light is blurred on the fundus. Thus, fundus reflection light that passes through the opening of the slit 15*b* in the light receiving optical system is reduced, and thus, the amount of received light is reduced.

Accordingly, the control unit 100 increases any one of the light intensity of illumination light output from the light sources 11*a* and 11*b* or the light sources 11*c* and 11*d*, the gain of the imaging element 28, and the exposure time, in the second imaging mode, as compared with the first imaging mode. Accordingly, deterioration in image quality due to blurring of the slit light emitted as illumination light on the fundus as a result of the processing of S7 is suppressed.

Then, the control unit 100 captures a fundus image after adjustment of the imaging conditions (S9). In the second imaging mode, in a state where the irradiation-side correction amount and the light receiving-side correction amount do not match each other, the fundus image is captured. Thus, in this example, even in a case where myopic is imaged, occurrence of artifacts is suppressed. During imaging, the diopter correction amount in the light receiving optical system 10*b* has a value immediately after the adjustment in the focus adjusting process (S5). Accordingly, since the fundus and the imaging plane conjugate with each other, defocus in the fundus image is suppressed. In the second imaging mode, since the slits 15*a* is disposed in a non-conjugate relationship with the fundus Er, the slit light emitted as the illumination light is blurred on the fundus. However, since any imaging condition among the light intensity of the illumination light, the gain of the imaging element 28 and the exposure time is increased compared with the first imaging mode, the fundus image having a proper dynamic range is easily obtained.

In a method for suppressing artifacts on a fundus image by image processing, a case where traces of the image processing is left in the image may be considered. However, in this example, since it is not necessary to perform image processing for suppressing artifacts, tissues of the fundus are more naturally drawn in a fundus image.

In the second imaging mode, as the intensity of illumination light or the exposure time is increased, it may be considered that load on an examinee is increased in comparison with the first imaging mode. However, since a time from imaging start (start of irradiation of illumination light for imaging) to imaging end is relatively short, the width of the load increase is considered to be relatively small. Accordingly, even in a case where a subject eye in which the degree of myopia is high is imaged, it is possible to capture a fundus image in which artifacts are suppressed without giving heavy burden on an examinee.

SECOND EXAMPLE

Figure 14:
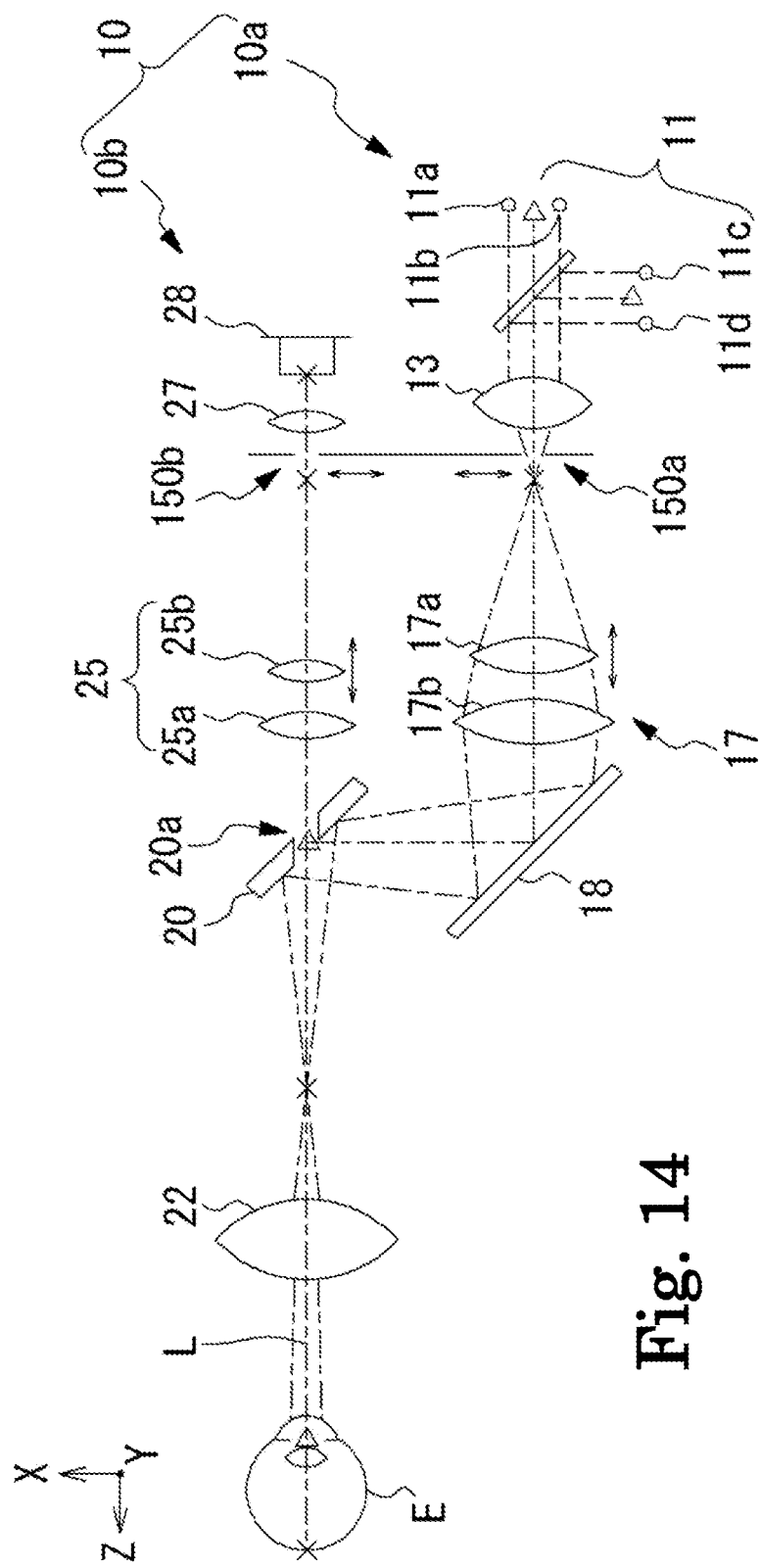
FIG. 14 is a diagram showing an optical system contained in the imaging unit, according to a second example.

Next, a second example in the fundus imaging apparatus according to a third embodiment will be described with reference to FIG. 14. Hereinafter, the second example will be described focusing on differences from the first example. In FIG. 14, the same reference numerals are given to the same configurations as in FIG. 2, and unless otherwise specified, detailed description thereof will be omitted. In FIG. 14, with respect to the optical system of the first example shown in FIG. 2, the anterior eye segment observation optical system 40 and the split index projection optical system 50 are not shown.

FIG. 14 shows an optical system of the fundus imaging apparatus 1 according to the second example. The fundus imaging apparatus 1 according to the second example has a configuration in which a position of slit-shaped members (an example of an aperture) is different from that in the first example. Specifically, the slit-shaped members 15*a* and 15*b* in the first example are disposed at the position that conjugates with the imaging plane. On the other hand, as shown in FIG. 14, slit-shaped members 150*a* and 150*b* in the second example are disposed in advance at a position different from the conjugate position of the imaging plane. In FIG. 14, both of the slit-shaped member 150*a* that is disposed in the irradiation optical system 10*a* and the slit-shaped member 150*b* that is disposed in the light receiving optical system 10*b* are disposed at positions different from the conjugate position of the imaging plane. Both of two slit-shaped members 150*a* and 150*b* are disposed on a positive diopter side with respect to the conjugate position of the imaging plane. Thus, an interval between the condensing position of reflected light on the objective lens and openings in two slit-shaped members 150*a* and 150*b* are secured. As a result, even though diopter correction in each of the irradiation optical system and the light receiving optical system is properly performed (without excess and deficiency of the refractive power of the subject eye), occurrence of artifacts based on the reflected light on the objective lens is suppressed. Further, as compared with the first example, the diopter correction amount is easily adjusted in a short time during imaging. Here, the invention is not necessarily limited thereto, and any one of two slit-shaped members 150*a* and 150*b* may be disposed at the conjugate position of the imaging plane.

MODIFICATION EXAMPLE

Hereinbefore, the description has been made on the basis of the embodiments, but in executing the present disclosure, it is possible to appropriately change the content of the embodiments.

<Switching Control in Accordance with Size of Pupil>

In the first example, the difference value between the irradiation-side correction amount and the light receiving-side correction amount is adjusted in accordance with the refractive power of the subject eye by the control unit 100. Here, with respect to the difference value, the size of the pupil may be considered. Further, the difference value may be adjusted in conjunction with a control operation set for each size of the pupil.

Figure 5:
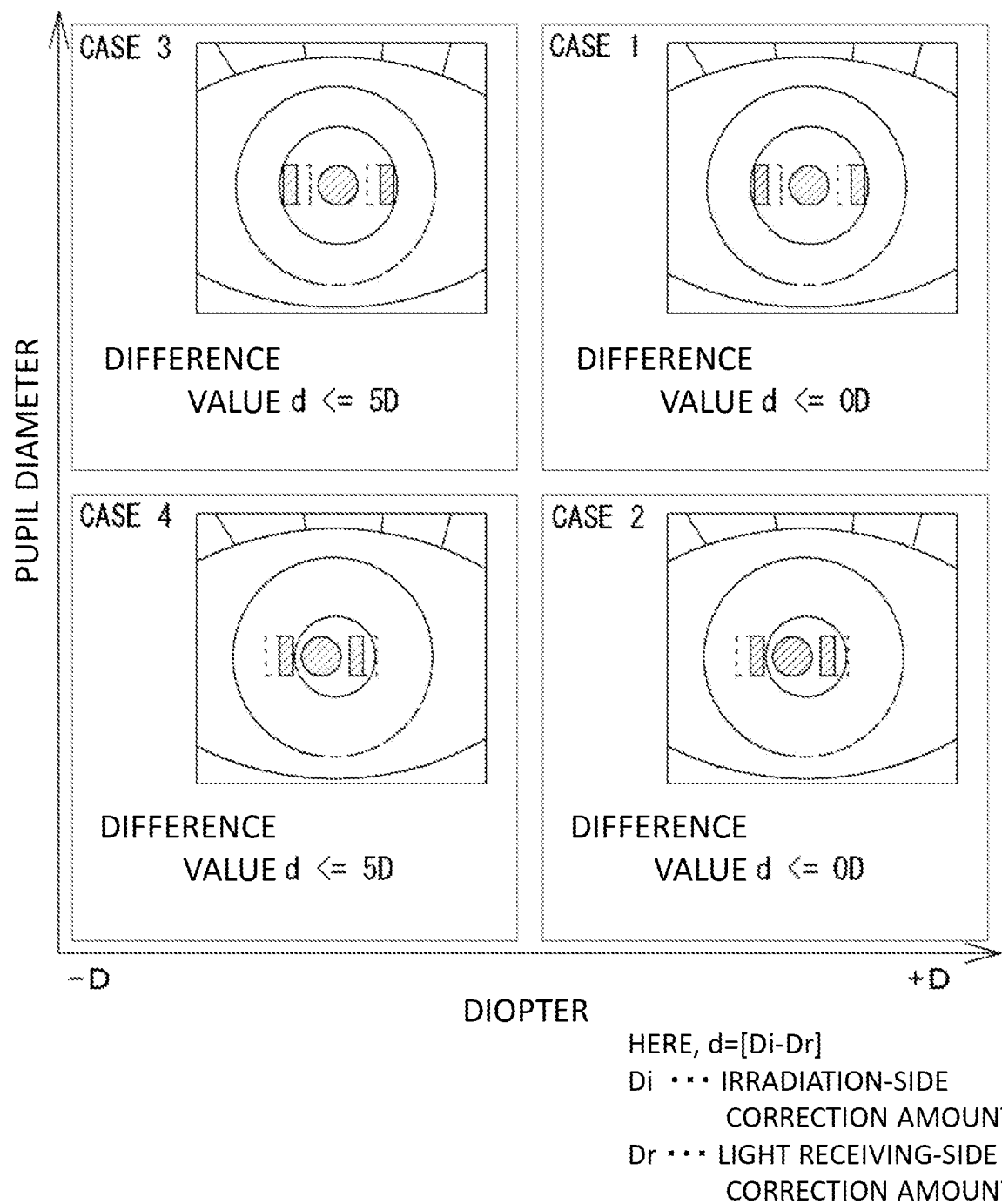
FIG. 5 is a diagram for explaining an adjustment control of a diopter correction value in consideration of the size of the pupil, in addition to the refractive power of the subject eye.
Figure 6:
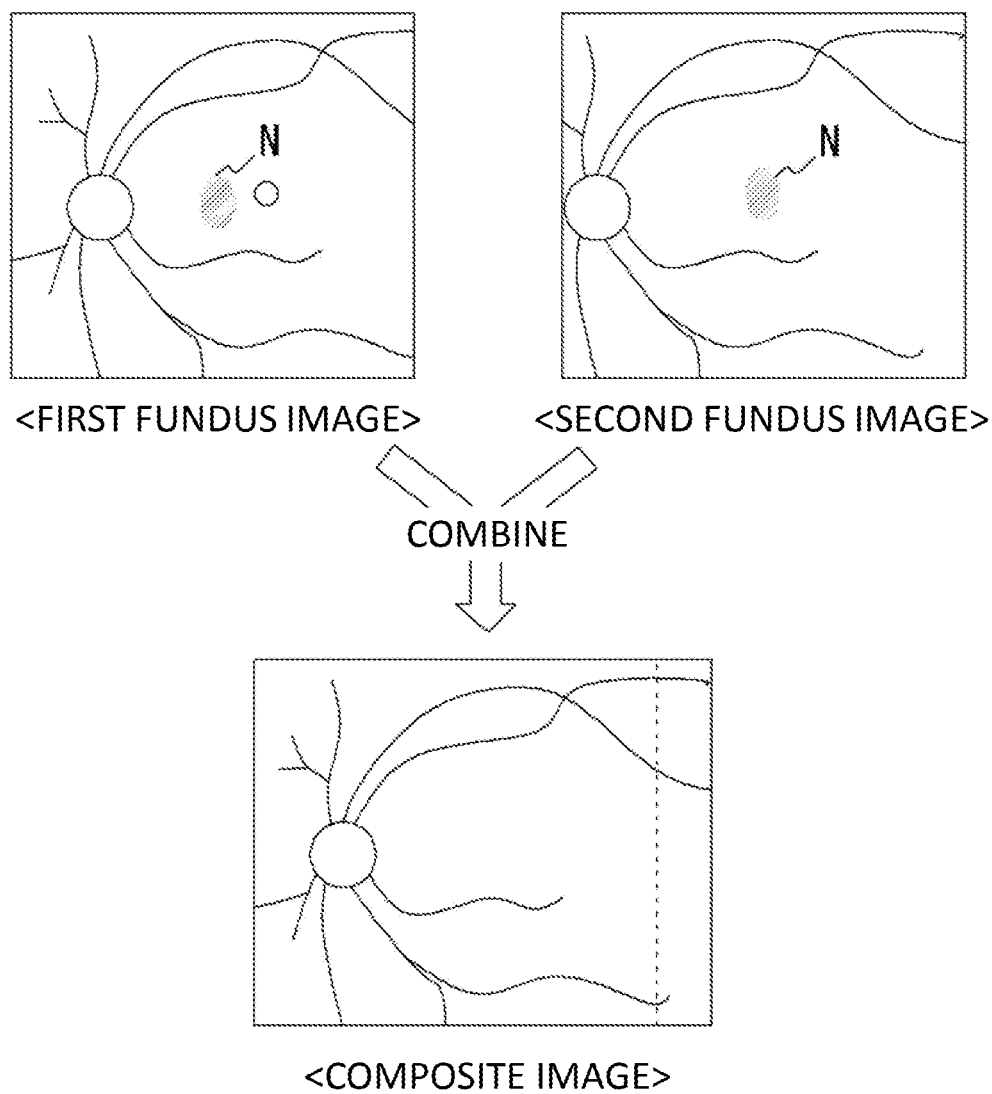
FIG. 6 is a diagram for explaining an outline of a second artifact suppressing process.

As an example, in the example shown in FIG. 5, in accordance with the size of the pupil (here, the pupil diameter) and the diopter value (refractive power) of the subject eye, the control of the apparatus splits into total four cases (Case 1 to Case 4). In other words, any one imaging mode is selected from four types of imaging modes in accordance with the size of the pupil and the diopter value. For example, the imaging mode may be selected on the basis of the size of the pupil detected from an anterior eye segment front image.

In the example shown in FIG. 5, (1) a clearance between a light projection region P and a light reception region R, (2) an alignment reference position in an XY direction, (3) a difference value between an irradiation-side correction amount and a light receiving-side correction amount are changed in accordance with the size of the pupil (here, the pupil diameter) and the diopter value of the subject eye (the refractive power) by the control unit 100. In accordance with comparison results of the size of the pupil (here, the pupil diameter) and the diopter value of the subject eye (the refractive power) with respective thresholds thereof, respective conditions are adjusted. As an example, "−12D" is used as the threshold value of the refractive power. "4 mm" is used as the threshold value of the pupil diameter. Both the thresholds are merely examples, and may be appropriately changed.

In order to change the clearance between the light projection region P and the light reception region R, a pair of second light sources may be provided at the centers between the light sources 11a and 11b and the optical axis L. In this case, by switching the light sources to be turned on, the clearance may be changed. Alternatively, the distance of the light sources 11a and 11b to the optical axis L may be changed. In the above example, the clearance is changed between a first interval and a second interval that are determined in advance. It is assumed that the second interval is narrower than the first interval.

In the above example, the alignment reference position is switched between a first reference position and a second reference position. The first reference position is a position where the center of the light reception region R and the corneal vertex (or the pupil center) match each other. The second reference position is a position having a positional relationship in which the center of the light reception region R and the corneal vertex (or the pupil center) deviates from each other by a predetermined distance, with reference to the first reference position.

The control unit 100 induces alignment on the basis of alignment deviation from the alignment reference position. Here, the induction of the alignment may be performed using a so-called auto-alignment method or a manual alignment method. In the automatic alignment method, the control unit 100 may drive-control the drive unit on the basis of the alignment deviation from the alignment reference position.

<Case 1 (Example of Invalid Mode)>

Case 1 is a case where the pupil diameter is larger than the threshold and the refractive power is on a positive diopter side with reference to the threshold. In this case, the respective conditions are set as follows.

(1) Clearance between light projection region P and light reception region R: first interval
(2) Alignment reference position in XY direction: first reference position
(3) Difference value d between irradiation-side correction amount and light receiving-side correction amount: 0D In Case 1, since an artifact does not easily occur due to reflection on the objective lens, the artifact suppressing process may not be performed. Further, since the pupil diameter is sufficiently large, even in a case where the clearance between the light projection region P and the light reception region R is made narrow or the deviation of the alignment reference position in the XY direction is not provided, it is possible to capture a good fundus image.

<Case 2 (Example of Valid Mode)>

Case 2 is a case where the pupil diameter is larger than the threshold and the refractive power is on a negative diopter side with reference to the threshold. In this case, the respective conditions are set as follows.

(1) Clearance between light projection region P and light reception region R: first interval
(2) Alignment reference position in XY direction: first reference position
(3) Difference value d between irradiation-side correction amount and light receiving-side correction amount: 5D In Case 2, since the refractive power is on the negative diopter side with respect to the threshold, as compared with Case 1, an artifact easily occurs. Accordingly, the irradiation-side correction amount and the light receiving-side correction amount are controlled to become different values. Accordingly, it is possible to suppress an artifact. Further, since the pupil diameter is sufficiently large, it is not necessary to make the clearance between the light projection region P and the light reception region R narrow, or to provide the deviation of the alignment reference position in the XY direction.

<Case 3 (Example of Valid Mode)>

Case 3 is a case where the pupil diameter is smaller than the threshold and the refractive power is on a positive diopter side with reference to the threshold. In this case, the respective conditions are set as follows.

(1) Clearance between light projection region P and light reception region R: second interval
(2) Alignment reference position in XY direction: second reference position
(3) Difference value d between irradiation-side correction amount and light receiving-side correction amount: 2.5D In case 3, since the pupil diameter is smaller than the threshold, the clearance between the light projection region P and the light reception region R is made narrow, and the alignment reference position in the XY direction is shifted with respect to the first reference position. In the above example, an artifact easily occurs by the above-mentioned controls. Accordingly, by setting the irradiation-side correction amount and the light receiving-side correction amount to different values, an artifact is suppressed. In other words, as compared with Case 1, a large value is given as the difference value d. The value of the difference value d in Case 3 is smaller than the difference value d in Case 2, but the value is not necessarily limited thereto. The value of the difference value d in each case may be appropriately set for each optical system.

<Case 4 (Example of Valid Mode)>

Case 4 is a case where the pupil diameter is smaller than the threshold and the refractive power is on a negative diopter side with reference to the threshold. In this case, the respective conditions are set as follows.

(1) Clearance between light projection region P and light reception region R: second interval
(2) Alignment reference position in XY direction: second reference position (3) Difference value d between irradiation-side correction amount and light receiving-side correction amount: 5D In case 4, since the pupil diameter is smaller than the threshold, the clearance between the light projection region P and the light reception region R is made narrow, and the alignment reference position in the XY direction is shifted with respect to the first reference position. The value of the difference value d between the irradiation-side correction amount and the light receiving-side correction amount employs the same value as in Case 2. Here, in a case where an artifact more easily occurs by the control according to the pupil diameter, a larger value compared with that in Case 2 may be set as the difference value d.

<Modification Example of Diopter Correction Optical System>

For example, in the above example, as the diopter correction optical systems 17 and 25, an optical system in which the diopter correction amount depending on the lens interval is set is shown an example. Here, the diopter correction optical system is not necessarily limited thereto, and may employ various optical systems. For example, in the case of the optical system shown in FIG. 2, as the slit-shaped member 15a instead of the lens 17a is displaced in the optical axis direction, it is possible to perform diopter correction in the irradiation optical system 10a. As the slit-shaped member 15a is displaced in the optical axis direction, the position of a condensing point K is displaced in the optical axis direction. Similarly, as the slit-shaped member 15b instead of the lens 25b is displaced in the optical axis direction, it is possible to perform diopter correction in the light receiving optical system 10b. In this case, the lens 27 and the imaging element 28 may be moved in conjunction with the slit-shaped member 25b. Furthermore, in this case, since it is difficult for one drive unit to perform a scan using the slit-shaped member 15a and a scan using the slit-shaped member 15b, each of the slit-shaped member 15a and the slit-shaped member 15b may be provided with a drive unit.

<Imaging Control in Fluorescent Imaging>

Further, for example, in the above-described respective embodiments, the fundus imaging apparatus does not capture only a fundus image based on fundus reflection light, but may also capture a fluorescence fundus image that is a fundus image based on fluorescence emitted from the fundus.

In this case, illuminating light from the irradiation optical system is emitted as excitation light. A wavelength range of the illumination light may be appropriately set in accordance with a desired fluorescent material. The fluorescent material may be a contrast agent (for example, indocyanine green, fluorescein, or the like), or may be a spontaneous fluorescent substance accumulated on the fundus (for example, lipofuscin).

In the light receiving optical system, the fluorescence from the fundus based on the excitation light is guided to the light receiving element. In a case where fluorescence imaging is performed, a barrier filter is disposed on an independent optical path of the light receiving optical system. The barrier filter has a spectral characteristic of shielding light having the same wavelength band as that of excitation light and passing fluorescence. Thus, among fundus reflection light of the excitation light and fluorescence from the fundus, the fluorescence is selectively received to the light receiving element. As a result, the fundus fluorescent image is favorably obtained. A drive unit for inserting or removing the barrier filter may be provided in the fundus imaging apparatus. Further, the insertion or removal of the barrier filter may be controlled by the control unit.

The control unit may perform switching of an imaging mode between a normal imaging mode and a fluorescent imaging mode. The normal imaging mode is set for capturing a fundus image based on fundus reflection light. The fluorescent imaging mode is set for capturing a fluorescent fundus image. The control unit may control the insertion or removal of the barrier filter in accordance with the imaging mode. In this case, the control unit retracts the barrier filter in the normal imaging mode. Further, the control unit inserts the barrier filter in the fluorescence imaging mode. Here, in the fluorescence imaging mode, reflected light on the objective lens in addition to fundus reflection light of excitation light is also shielded by the barrier filter. Thus, it is not necessary to perform the various artifact suppressing processes shown in the above embodiments, in the fluorescence imaging mode. Accordingly, in the fluorescent imaging mode, the artifact suppressing process may not be performed by the control unit, regardless of the refractive power of the subject eye. For example, in an apparatus that suppresses occurrence of artifacts by causing the diopter correction amount (irradiation-side correction amount) in the irradiation optical system and the diopter correction amount in the light receiving optical system (light receiving-side correction amount) to be different from each other, in the fluorescent imaging mode, each value is adjusted according to the refractive power so that the irradiation-side correction amount and the light receiving-side correction amount match each other.

In the present disclosure, as other embodiments, fundus imaging apparatuses B1 to B5, fundus imaging apparatuses C1 to C18, fundus imaging apparatuses D1 to D5, and fundus imaging apparatuses E1 to E8 described below are further disclosed.

<Fundus Imaging Apparatuses B1 to B5>

A fundus imaging apparatus B1 includes:

an imaging optical system including an irradiation optical system configured to irradiate a fundus of a subject eye with slit-shaped illumination light through an objective lens, a light receiving optical system configured to share the objective lens with the irradiation optical system and has an imaging plane on which a fundus image based on fundus reflection light of the illumination light is formed, and a scanning unit; and a diopter correction optical system configured to correct a diopter in the imaging optical system, in which the fundus image is captured in a state where a aperture is disposed at a position different from a fundus conjugate position relating to both of the objective lens and the diopter correction optical system.

In a fundus imaging apparatus B2, in the fundus imaging apparatus B1, the aperture is disposed in advance at a position different from both of the imaging plane and the conjugate position of the imaging plane.

In a fundus imaging apparatus B3, in the fundus imaging apparatus B2, the aperture is disposed in advance at a position spaced on a positive diopter side with respect to the conjugate position of the imaging plane.

In a fundus imaging apparatus B4, in the fundus imaging apparatus B2 or B3, in capturing the fundus image, the processor controls the diopter correction optical system to perform adjustment so that the imaging plane is disposed at the fundus conjugate position of the subject eye.

In a fundus imaging apparatus B5, in the fundus imaging apparatus B1, the diopter correction optical system is capable of independently adjusting an irradiation-side correction amount that is a diopter correction amount in the irradiation optical system and a light receiving-side correction amount that is a diopter correction amount in the light receiving optical system, respectively, and in capturing the fundus image, the processor controls the diopter correction optical system to set the irradiation-side correction amount and the light receiving-side correction amount to different values.

<Fundus Imaging Apparatuses C1 to C18>

A fundus imaging apparatus C1 that includes an irradiation optical system configured to irradiate a fundus of a subject eye with illumination light through an objective lens and a light receiving optical system configured to share the objective lens with the irradiation optical system and includes a light receiving element that receives fundus reflection light of the illumination light, and acquires a fundus image based on a signal from the light receiving element, includes:

a diopter correction optical system configured to independently adjust an irradiation-side correction amount that is a diopter correction amount in the irradiation optical system and a light receiving-side correction amount that is a diopter correction amount in the light receiving optical system, respectively; and a processor configured to control the diopter correction optical system to set the irradiation-side correction amount and the light receiving-side correction amount to different values.

In a fundus imaging apparatus C2, in the fundus imaging apparatus B5 or C1, the processor adjusts the light receiving-side correction amount in accordance with the refractive power of the subject eye, and sets the irradiation-side correction amount so that a condensing position of the illumination light through the diopter correction optical system is disposed at a position more distant from the objective lens with respect to an intermediate image plane of the fundus formed through the objective lens.

In a fundus imaging apparatus C3, in the fundus imaging apparatus B5 or C2, the processor adjusts the light receiving-side correction amount in accordance with the refractive power of the subject eye, and sets the irradiation-side correction amount to a value of which an absolute value is smaller than that of the light receiving-side correction amount.

In a fundus imaging apparatus C4, in any one of the fundus imaging apparatuses B5, and C1 to C3, the processor performs switching of an imaging mode between a first imaging mode and a second imaging mode in which a difference value between the irradiation-side correction amount and the light receiving-side correction amount is adjusted to a value larger than that in the first imaging mode to capture the fundus image, in accordance with the refractive power of the subject eye.

In a fundus imaging apparatus C5, in the fundus imaging apparatus C4, the processor adjusts the difference value in consideration of the size of the pupil of the subject eye.

In a fundus imaging apparatus C6, in the fundus imaging apparatus C4 or C5, the processor makes the irradiation-side correction amount and the light receiving-side correction amount match each other to capture the fundus image in the first imaging mode, and makes the irradiation-side correction amount and the light receiving-side correction amount different from each other to capture the fundus image in the second imaging mode.

In a fundus imaging apparatus C7, in any one of the fundus imaging apparatuses C4 to C6, the refractive power of the subject eye is divided into a first range and a second range on a negative diopter side with respect to the first range, and the processor switches the imaging mode to the first imaging mode in a case where the refractive power of the subject eye is in the first range, and switches the imaging mode to the second imaging mode in a case where the refractive power of the subject eye is in the second range.

In a fundus imaging apparatus C8, in any one of the fundus imaging apparatuses C2 to C7, the fundus imaging apparatus further includes a refractive power information acquisition unit configured to acquire refractive power information on the refractive power of the subject eye, the processor sets the irradiation-side correction amount and the light receiving-side correction amount on the basis of the refractive power information.

In a fundus imaging apparatus C9, in the fundus imaging apparatus C8, the refractive power information acquisition unit detects a focusing state in the light receiving optical system, and acquires the refractive power information on the basis of a detection result of the focusing state.

In a fundus imaging apparatus C10, in any one of the fundus imaging apparatuses B5, and C1 to C9, the fundus imaging apparatus further includes an optical path coupler that is disposed between the objective lens and the light receiving element and couples an optical path of the irradiation optical system and an optical path of the light-receiving optical system, the diopter correction optical system includes a first diopter correction optical system that is disposed on one optical path among the optical paths of the irradiation optical system and the light receiving optical system, and a second diopter correction optical system that is disposed on the other optical path with respect to the one optical path or a common optical path of the irradiation optical system and the light-receiving optical system, and the processor individually controls the first diopter correction optical system and the second diopter correction optical system to set the irradiation-side correction amount and the light receiving-side correction amount to different values.

In a fundus imaging apparatus C11, in the fundus imaging apparatus C10, the fundus imaging apparatus further includes a first drive unit configured to drive at least one optical element included in the first diopter correction optical system, and a second drive unit configured to drive at least one optical element included in the second diopter correction optical system, in which the control unit independently controls the first drive unit and the second drive unit.

In a fundus imaging apparatus C12, in any one of the fundus imaging apparatuses C1 to C11, the irradiation optical system forms a local illumination region in a part of an imaging range on the fundus, and the fundus imaging apparatus further includes:

a harmful light removing unit configured to be disposed on the optical path of the light receiving optical system with the diopter correction optical system being interposed between the objective lens and the harmful light removing unit, cause the fundus reflection light from the local imaging region that is a part of the imaging range to be received to the light receiving element, and remove light from a region other than the imaging region; and a scanning unit configured to synchronously scan the local illumination region and the local imaging region on the fundus.

In a fundus imaging apparatus C13, in the fundus imaging apparatus B5 or C12, the harmful light removing unit is disposed at a position that conjugates with the fundus with respect to at least the objective lens and the diopter correction optical system, in a state where the light receiving-side correction amount depending on the refractive power of the subject eye is set.

In a fundus imaging apparatus C14, in any one of the fundus imaging apparatuses B5, and C12 to C13, the diopter correction optical system includes a telecentric optical system configured to maintain the height of an image on an image side, regardless of a combination of the irradiation-side correction amount and the light receiving-side correction amount, in each of the irradiation optical system and the light receiving optical system.

In a fundus imaging apparatus C15, in any one of the fundus imaging apparatuses B5, and C12 to C14, the local illumination region and the local imaging region are respectively formed in a slit shape.

In a fundus imaging apparatus C16, in the fundus imaging apparatus C15, a first slit-shaped member having a slit-shaped opening is provided on the optical path of the irradiation optical system, the harmful light removing unit is a second slit-shaped member that has the slit-shaped opening and guides light passing through the opening to the light receiving element, and the scanning unit includes the first slit-shaped member and the second slit-shaped member, and a drive unit that moves the first slit-shaped member and the second slit-shaped member in a direction that intersects an optical axis.

In a fundus imaging apparatus C17, in the fundus imaging apparatus C15, the scanning unit includes a first scanning unit that is an optical scanner disposed on the illumination optical system, and a second scanning unit that is a separate body from the first scanning unit and is disposed on the light-receiving optical system, and the light receiving element is a CMOS device, and as line exposure by a rolling shutter function of the CMOS device is synchronized with scan by the first scanning unit, the light receiving element serves as the harmful light removing unit and the second scanning unit.

In a fundus imaging apparatus C18, in any of the fundus imaging apparatuses B5, and C12 to C14, the local illumination region and the local imaging region are respectively formed in a spot shape.

<Fundus Imaging Apparatuses D1 to D5>

A fundus imaging apparatus D1 includes:

an imaging optical system including an irradiation optical system configured to irradiate a fundus of a subject eye with illumination light through an objective lens and a light receiving optical system configured to share the objective lens with the irradiation optical system and include a light receiving element that receives fundus reflection light of the illumination light;

a processor that controls one or both of the irradiation optical system and the light receiving optical system to change an imaging condition, and acquires at least two fundus images on the basis of a signal from the light receiving element; and an imaging processor that combines at least the two fundus images having different imaging conditions to obtain a composite image.

In a fundus imaging apparatus D2, in the fundus imaging apparatus D1, the processor acquires the two fundus images that become a base of the composite image, without changing a positional relationship between an optical axis of the imaging optical system and a visual axis of the subject eye.

In a fundus imaging apparatus D3, in the fundus imaging apparatus D1 or D2, the imaging optical system includes a diopter correction optical system, and the processor changes a diopter correction amount in the diopter correction optical system as the imaging condition, in each imaging, by controlling the diopter correction optical system, in capturing at least the two fundus images that become the base of the composite image.

In a fundus imaging apparatus D4, in the fundus imaging apparatus D1 or D2, the processor changes a separation state between the fundus reflection light and harmful light due to illumination light reflected from the objective lens, in each imaging, by controlling the imaging optical system, in capturing at least the two fundus images that become the base of the composite image.

In a fundus imaging apparatus D5, in any one of the fundus imaging apparatuses D1 to D4, the illumination light is visible light, and the processor executes a consecutive imaging process of capturing two fundus images in a predetermined interval, in the order of the second fundus image and the first fundus image, in order to acquire the two fundus images that become the base of the composite image.

<Fundus Imaging Apparatuses E1 to E8>

A fundus imaging apparatus E1 includes an imaging optical system including an irradiation optical system configured to irradiate a fundus of a subject eye with illumination light and a light receiving optical system including an imaging element that receives return light of the illumination light from the fundus, and acquires a fundus image that is a front image of the fundus based on a light reception signal from the imaging element, the imaging optical system includes:

an optical element that forms a local imaging region in a slit shape; and a scanning unit configured to scan the imaging region with respect to the fundus, in which the optical element is able to change the width of the imaging region to any one of a first width and a second width wider than the first width, and the processor acquires a first fundus image as a captured image based on a scan in the imaging region with the first width, and acquires a second fundus image as a captured image based on a scan in the imaging region with the second width.

In a fundus imaging apparatus E2, in the fundus imaging apparatus E1, the processor changes a wavelength of the illumination light for each image, to acquire a fundus color image as the first fundus image and acquire a fundus fluorescence image as the second fundus image.

In a fundus imaging apparatus E3, in the fundus imaging apparatus E1, the processor selectively acquires any one of the first fundus image and the second fundus image on the basis of information relating to the size of the pupil of the subject eye.

In a fundus imaging apparatus E4, in any one of the fundus imaging apparatuses E1 to E3, the optical element is a rotating body in which a plurality of slit openings are disposed side by side on one circumference, the scanning unit is an optical chopper that includes the rotating body and continuously crosses the plurality of slit openings with respect to an optical path of the illumination light or the return light by rotationally driving the rotating body, the rotating body includes a first area where one or two or more first slit openings corresponding to the first width are continuously arranged, and a second area where one or two or more second slit openings corresponding to the second width are continuously arranged, and the processor acquires the first fundus image on the basis of a signal from the imaging element exposed in a first period during which the first area passes through the optical path, and acquires the second fundus image on the basis of a signal from the imaging element exposed in a second period during which the second area passes through the optical path.

In a fundus imaging apparatus E5, in the fundus imaging apparatus E4, the processor further controls the optical chopper, and sequentially acquires the fundus image as an observation image at a constant frame rate based on the signal from the imaging element while continuously rotating the rotating body.

In a fundus imaging apparatus E6, in the fundus imaging apparatus E5, the processor alternately acquires a first observation image based on the signal from the imaging element exposed in the first period and a second observation image based on the signal from the imaging element exposed in the second period, as the observation image, whenever the first period and the second period are switched, and in acquiring the observation image, the processor reduces any one of a light intensity of the illumination light and a gain of the signal from the imaging element, in the second period, compared with the first period.

In a fundus imaging apparatus E7, in the fundus imaging apparatus E6, the processor acquires each frame of the observation image based on a signal from the imaging element exposed in both of at least a part of the first period and at least a part of the second period.

In a fundus imaging apparatus E8, in any of the fundus imaging apparatuses E1 to E7, the imaging optical system has a diopter correction optical system for correcting an error of a diopter in the subject eye, and the processor selectively acquires any one of the first fundus image and the second fundus image in accordance with a diopter correction amount in the diopter correction optical system.

What is claimed is:

1. A fundus imaging apparatus that includes an irradiation optical system configured to irradiate a fundus of a subject eye with illumination light through an objective lens, and a light receiving optical system configured to share the objective lens with the irradiation optical system and including a light receiving element that receives fundus reflection light of the illumination light, and acquires a fundus image based on a signal from the light receiving element, the fundus imaging apparatus comprising:
a diopter correction optical system configured to independently adjust an irradiation-side correction amount that is a diopter correction amount in the irradiation optical system and a light receiving-side correction amount that is a diopter correction amount in the light receiving optical system, respectively; and
a processor configured to control the diopter correction optical system to set the irradiation-side correction amount and the light receiving-side correction amount to different values such that generation of artifacts due to reflection of the illumination light on the objective lens is suppressed.

2. The fundus imaging apparatus according to claim 1, wherein the processor adjusts the light receiving-side correction amount in accordance with the refractive power of the subject eye, and sets the irradiation-side correction amount so that a condensing position of the illumination light through the diopter correction optical system is disposed at a position more distant from the objective lens with respect to an intermediate image plane of the fundus formed through the objective lens.

3. The fundus imaging apparatus according to claim 1, wherein the processor performs switching of an imaging mode between a first imaging mode and a second imaging mode in which a difference value between the irradiation-side correction amount and the light receiving-side correction amount is adjusted to a value larger than that in the first imaging mode to capture the fundus image, in accordance with the refractive power of the subject eye.

4. The fundus imaging apparatus according to claim 3, wherein the processor makes the irradiation-side correction amount and the light receiving-side correction amount match each other to capture the fundus image in the first imaging mode, and makes the irradiation-side correction amount and the light receiving-side correction amount different from each other to capture the fundus image in the second imaging mode.

5. The fundus imaging apparatus according to claim 1, further comprising:
an optical path coupler that is disposed between the objective lens and the light receiving element and couples an optical path of the irradiation optical system and an optical path of the light-receiving optical system,
wherein the diopter correction optical system includes a first diopter correction optical system that is disposed on one optical path among the optical paths of the irradiation optical system and the light receiving optical system, and a second diopter correction optical system that is disposed on the other optical path with respect to the one optical path or a common optical path of the irradiation optical system and the light-receiving optical system, and
the processor individually controls the first diopter correction optical system and the second diopter correction optical system to set the irradiation-side correction amount and the light receiving-side correction amount to different values.

6. The fundus imaging apparatus according to claim 5, further comprising:

a first drive unit configured to drive at least one optical element included in the first diopter correction optical system; and a second drive unit configured to drive at least one optical element included in the second diopter correction optical system, wherein the control unit independently controls the first drive unit and the second drive unit.

7. The fundus imaging apparatus according to claim 1, wherein the irradiation optical system foil is a local illumination region in a part of an imaging range on the fundus, and the fundus imaging apparatus further comprises:

a harmful light removing unit configured to be disposed on the optical path of the light receiving optical system with the diopter correction optical system being interposed between the objective lens and the harmful light removing unit, cause the fundus reflection light from the local imaging region that is a part of the imaging range to be received to the light receiving element, and remove light from a region other than the imaging region; and a scanning unit configured to synchronously scan the local illumination region and the local imaging region on the fundus.

8. The fundus imaging apparatus according to claim 7, wherein the diopter correction optical system includes a telecentric optical system configured to maintain the height of an image on an image side, regardless of a combination of the irradiation-side correction amount and the light receiving-side correction amount, in each of the irradiation optical system and the light receiving optical system.

9. The fundus imaging apparatus according to claim 7, wherein the local illumination region and the local imaging region are respectively formed in a slit shape.

* * * * *